US008084491B2

(12) United States Patent
Shapira et al.

(10) Patent No.: US 8,084,491 B2
(45) Date of Patent: Dec. 27, 2011

(54) TREATMENTS FOR WOUND HEALING

(75) Inventors: Nathan Andrew Shapira, Atlanta, GA (US); Mary Catherine Lessig, Seattle, WA (US); Daniel John Driscoll, Gainesville, FL (US)

(73) Assignee: Novodermix International Limited, Road Town, Tortola (VG)

( * ) Notice: Subject to any disclaimer, the term of this patent is extended or adjusted under 35 U.S.C. 154(b) by 0 days.

(21) Appl. No.: 11/830,906

(22) Filed: Jul. 31, 2007

(65) Prior Publication Data

US 2008/0021094 A1   Jan. 24, 2008

Related U.S. Application Data

(63) Continuation of application No. 11/013,259, filed on Dec. 15, 2004, now abandoned, which is a continuation of application No. 09/997,447, filed on Nov. 30, 2001, now abandoned.

(60) Provisional application No. 60/250,113, filed on Nov. 30, 2000.

(51) Int. Cl.
*A61K 31/35* (2006.01)

(52) U.S. Cl. ........................................................ 514/454

(58) Field of Classification Search ........................ None
See application file for complete search history.

(56) References Cited

U.S. PATENT DOCUMENTS

| 892,088 | A | 6/1908 | Rich |
|---|---|---|---|
| 4,513,006 | A | 4/1985 | Maryanoff et al. |
| 5,384,327 | A | 1/1995 | Costanzo et al. |
| 5,498,629 | A | 3/1996 | Costenzo et al. |
| 5,507,775 | A | 4/1996 | Ger et al. |
| 5,512,041 | A | 4/1996 | Bogart |
| 5,512,291 | A | 4/1996 | Li |
| 5,519,020 | A | 5/1996 | Smith et al. |
| 5,520,926 | A | 5/1996 | Ferguson |
| 5,522,794 | A | 6/1996 | Ewall |
| 5,525,335 | A | 6/1996 | Kitahara et al. |
| 5,571,521 | A | 11/1996 | Lasker |
| 5,578,022 | A | 11/1996 | Scherson et al. |
| 5,578,310 | A | 11/1996 | M'Timkulu et al. |
| 5,602,183 | A | 2/1997 | Martin et al. |
| 5,603,946 | A | 2/1997 | Constantine |
| 5,610,148 | A | 3/1997 | Brown |
| 5,614,561 | A | 3/1997 | Martin |
| 5,629,292 | A | 5/1997 | Rodgers et al. |
| 5,631,019 | A | 5/1997 | Marx |
| 5,632,727 | A | 5/1997 | Tipton et al. |
| 5,633,285 | A | 5/1997 | Martin |
| 5,641,814 | A | 6/1997 | Martin |
| 5,646,190 | A | 7/1997 | Martin |
| 5,648,380 | A | 7/1997 | Martin |
| 5,652,274 | A | 7/1997 | Martin |
| 5,654,461 | A | 8/1997 | Choi et al. |
| 5,658,956 | A | 8/1997 | Martin et al. |
| 5,658,957 | A | 8/1997 | Martin |
| 5,662,904 | A | 9/1997 | Ferguson et al. |
| 5,662,924 | A | 9/1997 | Rhodes |
| 5,663,208 | A | 9/1997 | Martin |
| 5,667,501 | A | 9/1997 | Fowler et al. |
| 5,674,912 | A | 10/1997 | Martin |
| 5,685,834 | A | 11/1997 | Barth |
| 5,690,795 | A | 11/1997 | Rosenstein et al. |
| 5,692,302 | A | 12/1997 | Martin et al. |
| 5,705,477 | A | 1/1998 | Sporn et al. |
| 5,707,647 | A | 1/1998 | Dunn et al. |
| 5,713,842 | A | 2/1998 | Kay |
| 5,716,337 | A | 2/1998 | McCabe et al. |
| 5,716,935 | A | 2/1998 | Rodgers et al. |
| 5,735,812 | A | 4/1998 | Kardy |
| 5,753,694 | A | 5/1998 | Shank |
| 5,759,570 | A | 6/1998 | Arnold |
| 5,760,006 | A | 6/1998 | Shank et al. |
| 5,780,048 | A | 7/1998 | Lee |
| 5,804,213 | A | 9/1998 | Rolf |
| 5,807,300 | A | 9/1998 | Nix, Jr. |
| 5,807,341 | A | 9/1998 | Heim |
| 5,834,432 | A | 11/1998 | Rodgers et al. |
| 5,856,245 | A | 1/1999 | Caldwell et al. |
| 5,856,364 | A | 1/1999 | Martin |
| 5,863,938 | A | 1/1999 | Martin |
| 5,874,479 | A | 2/1999 | Martin |
| 5,876,743 | A | 3/1999 | Ibsen et al. |
| 5,892,088 | A | 4/1999 | Choi et al. |
| 5,897,516 | A | 4/1999 | Kadash et al. |
| 5,902,600 | A | 5/1999 | Woller et al. |
| 5,914,125 | A | 6/1999 | Andrews et al. |
| 5,955,430 | A | 9/1999 | Rodgers et al. |
| 5,960,795 | A | 10/1999 | Schultz |

(Continued)

FOREIGN PATENT DOCUMENTS

EP   0138441   9/1984

(Continued)

OTHER PUBLICATIONS

The Merck Manual, 17th edition (1999), p. 1938.*
Stedman's Medical Dictionary (1995), p. 900.*
Burton, L. and Harden, C., "Effect of Topiramate on Attention," *Epilepsy Research*, 1997, pp. 29-32, vol. 27, Pub: Elsevier Science B.V.
Carrel, Al., et al., "Growth Hormone Improves Body Composition, Fat Utilization, Physical Strength and Agility, and Growth in Prader-Willi Syndrome: A Controlled Study," *J. Pediatrics*, 1999, pp. 215-221, vol. 134, Pub: Mosby, Inc.
Crawford, P., "An Audit of Topiramate Use in a General Neurology Clinic," *Seizure*, 1998, pp. 207-211, vol. 7, Pub: British Epilepsy Association.
Davanzo, P.A. and King, B.H., "Open Trial of Lamotrigine in the Treatment of Self-Injurious Behavior in an Adolescent with Profound Mental Retardation," *J. of Child & Adolescent Psychopharmacology*, 1996, pp. 273-279, vol. 6, No. 4, Pub: Mary Ann Liebert, Inc.

(Continued)

*Primary Examiner* — Phyllis G. Spivack

(57) ABSTRACT

The subject invention provides methods of promoting wound healing comprising the administration of a therapeutically effective amount of a composition comprising topiramate. Compositions may administered to a wound site via a salve, ointment, or as a component of a bandage or bioadhesive applied to the site of injury.

3 Claims, 13 Drawing Sheets
(6 of 13 Drawing Sheet(s) Filed in Color)

U.S. PATENT DOCUMENTS

| | | | |
|---|---|---|---|
| 5,968,001 | A | 10/1999 | Freeman |
| 5,972,332 | A | 10/1999 | Rees et al. |
| RE36,370 | E | 11/1999 | Li |
| 5,977,428 | A | 11/1999 | Bozigian et al. |
| 5,981,606 | A | 11/1999 | Martin |
| 5,989,577 | A | 11/1999 | Hoath et al. |
| 5,998,692 | A | 12/1999 | Gilding |
| 6,022,556 | A | 2/2000 | Hardy |
| 6,025,150 | A | 2/2000 | Livant |
| 6,033,684 | A | 3/2000 | Norcia |
| 6,051,249 | A | 4/2000 | Samuelsen |
| 6,071,537 | A | 6/2000 | Shank |
| 6,087,549 | A | 7/2000 | Flick |
| 6,093,388 | A | 7/2000 | Ferguson |
| 6,096,709 | A | 8/2000 | Rodgers et al. |
| 6,124,273 | A | 9/2000 | Drohan et al. |
| 6,132,759 | A | 10/2000 | Schacht et al. |
| 6,136,341 | A | 10/2000 | Petito |
| 6,142,982 | A | 11/2000 | Hunt et al. |
| 6,143,037 | A | 11/2000 | Goldstein et al. |
| 6,323,236 | B2 | 11/2001 | McElroy |
| 6,462,084 | B1 | 10/2002 | Dewey et al. |
| 6,583,172 | B1 * | 6/2003 | Shank .......................... 514/439 |
| 2002/0082222 | A1 | 6/2002 | Shapira et al. |
| 2002/0137903 | A1 | 9/2002 | Ellsworth et al. |
| 2004/0014681 | A1 | 1/2004 | Ryback |

FOREIGN PATENT DOCUMENTS

| | | |
|---|---|---|
| WO | WO 98/00123 | 1/1998 |
| WO | WO 98/00129 | 1/1998 |
| WO | WO 98/00131 | 1/1998 |
| WO | WO 98/15270 | 4/1998 |
| WO | WO 00/00130 | 1/2000 |
| WO | WO 00/10610 | 3/2000 |
| WO | WO 00/23059 | 4/2000 |
| WO | WO 00/28945 | 5/2000 |
| WO | WO 00/44374 | 8/2000 |
| WO | WO 00/48549 | 8/2000 |
| WO | WO 00/50020 | 8/2000 |
| WO | WO 00/76493 | 12/2000 |
| WO | WO 02/43731 | 6/2002 |

OTHER PUBLICATIONS

Donovan, S.J., et al., "Divalproex Treatment for Youth with Explosive Temper and Mood Lability: A Double-Blind, Placebo-Controlled Crossover Design," *Am J Psychiatry*, 2000, pp. 818-820, vol. 157, No. 5, Pub: Unknown.

Dykens, E.M. and Hodapp, R.M., "Treatment Issues in Genetic Mental Retardation Syndromes," *Professional Psychology: Research & Practice*, 1997, pp. 263-270, vol. 28, No. 3, Pub: American Psychological Association, Inc.

Emerson, E., et al., "The Prevalence of Challenging Behaviors: A Total Population Study," *Res. In Developmental Disabilities*, 2001, pp. 77-93, vol. 22, Pub: Elsevier Science Ltd.

Faught, E., et al., "Topiramate Placebo-Controlled Dose-Ranging Trial in Refractory Partial Epilepsy Using 200-, 400-, and 600-mg Daily Dosages," *Neurology*, 1996, pp. 1684-1690, vol. 46, Pub: American Academy of Neurology.

Gerber, P.E., et al., "Factors Associated with Behavioral and Cognitive Abnormalities in Children Receiving Topiramate," *Pediatric Neurology*, 2000, pp. 200-203, vol. 22, No. 3, Pub: Elsevier Science Inc.

Glenn, C.C., et al., "Genomic Imprinting: Potential Function and Mechanisms Revealed by the Prader-Willi and Angelman Syndromes," *Molecular Human Reproduction*, 1997, pp. 321-332, vol. 3, No. 4, Pub: European Society for Human Reproduction and Embryology.

Goldsmith, T., et al., "Conceptual Foundations of Obsessive-Compulsive Spectrum Disorders," *Obsessive-Compulsive Disorder: Theory, Research, and Treatment*, 1998, pp. 397-425, Part III, Ch. 17, Pub: The Guilford Press, New York London, Div. Of Guilford Publications, Inc. (eds. Swinson, R.P., et al.), New York.

Gupta, B.K., et al., "Carbamazepine for Intermittent Explosive Disorder in a Prader-Willi Syndrome Patient," *J Clin Psychiatry*, 1987, p. 423, vol. 48, No. 10, Pub: Unknown.

Haller, R. And Hinterhuber, H., "Treatment of Pathological Gambling with Carbamazepine," *Pharmacopsychiatry*, 1994, p. 129, vol. 27, No. 3, Pub: Georg Thieme Verlag Stuttgart, New York.

Ireland, J.L., "A Descriptive Analysis of Self-Harm Reports Among a Sample of Incarcerated Adolescent Males," *J. Adolescence*, 2000, pp. 605-613, vol. 23, Pub: Association for Professionals in Services for Adolescents.

Jones, M.W., "Topiramate—Safety and Tolerability," *Can. J. Neural. Sci.*, 1998, pp. S13-S15, vol. 25, Suppl. 3, Pub: Unknown, Canada.

Kmetz, G.F., et al., "Response of Kleptomania and Mixed Mania to Valproate," *Am J Psychiatry*, 1997, pp. 580-581, vol. 154, No. 4, Pub: Unknown.

Ko, S.M., "Under-Diagnosed Psychiatric Syndrome II: Pathologic Skin Picking," *Annals Academy of Medicine Singapore*, 1999, pp. 557-559, vol. 28, No. 4, Pub: Unknown, Singapore.

Lindgren, a.G., et al., "Effects of Growth Hormone Treatment on Growth and Body Composition in Prader-Willi Syndrome: A Preliminary Report. The Swedish National Growth Hormone Advisory Group," *Acta Paediatr Suppl*, 1997, pp. 60-62, vol. 423, Pub: Scandinavian University Press.

Marcotte, D., "Use of Topiramate, A New Anti-Epileptic as a Mood Stabilizer," *Journal of Affective Disorders*, 1998, pp. 245-251, vol. 50, Pub: Elsevier Science B.V.

Martin, A., et al., "Prader-Willi Syndrome," *Clinical Case Conference*, 1998, pp. 1265-1273, Pub: Unknown.

Martin, R., et al., "Cognitive Effects of Topiramate, Gabapentin, and Lamotrigine in Healthy Young Adults," *Neurology*, 1999, pp. 321-327, vol. 52, Pub: American Academy of Neurology.

McElroy, S.L., et al., "Open-Label Adjunctive Topiramate in the Treatment of Bipolar Disorders," *Biol. Psychiatry*, 2000, pp. 1025-1033, vol. 47, Pub: Society of Biological Psychiatry.

Mikati, M.A., et al., "Gabapentin in the Treatment of Refractory Partial Epilepsy in Children with Intellectual Disability," *J. Intellectual Disability Research*, 1998, pp. 57-62, vol. 42, Suppl. 1, Pub: Blackwell Science Ltd.

Mitchell, W.G., et al., "Effects of Antiepileptic Drugs on Reaction Time, Attention, and Impulsivity in Children," *Pediatrics*, 1993, pp. 101-105, vol. 91, No. 1, Pub: American Academy of Pediatrics.

Mitchell, W.G., et al., "Reaction Time, Attention, and Impulsivity in Epilepsy," *Pediatric Neurology*, 1992, pp. 19-24, vol. 8, No. 1, Pub: Unknown.

Neziroglu, F., et al., "Skin Picking as a Form of Self-Injurious Behavior," *Psychiatric Annals*, 2001, pp. 549-555, vol. 31, No. 9, Pub: Unknown.

Persinger, M.A., "Subjective Improvement Following Treatment with Carbamazepine (Tegretol) for a Subpopulation of Patients with Traumatic Brain Injuries," *Perceptual and Motor Skills*, 2000, pp. 37-40, vol. 90, Pub: Perceptual and Motor Skills 2000.

Privitera, M., et al., "Topiramate Placebo-Controlled Dose-Ranging Trial in Refractory Partial Epilepsy Using 600-, 800-, and 1,000-mg Daily Dosages," *Neurology*, 1996, pp. 1678-1683, vol. 46, Pub: American Academy of Neurology.

Roach, E.S., et al., "Carbamazepine Trial for Lesch-Nyhan Self-Mutilation," *J. Child Neurology*, 1996, pp. 476-478, vol. 11, No. 6, Pub: Unknown.

Rosenfeld, W.E., et al., "Comparison of the Steady-State Pharmacokinetics of Topiramate and Valproate in Patients with Epilepsy During Monotherapy and Concomitant Therapy," *Epilepsia*, 1997, pp. 324-333, vol. 38, No. 3, Pub: Lippincott-Raven Publishers, Philadelphia, © Int'l League Against Epilepsy.

Ruedrich, S., et al., "Effect of Divalproex Sodium on Aggression and Self-Injurious Behaviour in Adults with Intellectual Disability: A Retrospective Review," *Journal of Intellectual Disability Research*, 1999, pp. 105-111, vol. 43, part 2, Pub: Blackwell Science Ltd.

Selikowitz, M., et al., "Fenfluramine in Prader-Willi Syndrome: A Double Blind, Placebo Controlled Trial," 1989, Pub: Unknown, Australia.

Shapira, N. A., et al., "Open-Label Pilot Study of Topiramate in Adults with Prader-Willi Syndrome," *ACNP—American College of Neuropsychopharmacology—Scientific Abstract: 39th Annual Meeting*, 2000, p. 271, Poster Session II, #71—abstract and poster, Pub: American College of Neuropsychopharmacology.

Silva, R.R., et al., "Carbamazepine Use in Children and Adolescents with Features of Attention-Deficit Hyperactivity Disorder: A Meta-Analysis," *J. Am. Acad. Child Adolesc. Psychiatry*, 1996, pp. 352-358, vol. 35, No. 3, Pub: American Academy of Child and Adolescent Psychiatry.

Thompson, P.J., et al., "Effects of Topiramate on Cognitive Function," *J Neurol Neurosurg Psychiatry*, 2000, pp. 636-641, vol. 69, Pub: Unknown, United Kingdom.

Wilhelm, S., et al., "Self-Injurious Skin Picking: Clinical Characteristics and Comorbidity," *J Clin Psychiatry*, 1999, pp. 454-459, vol. 60, No. 7, Pub: Unknown, Massachusetts.

Martin "Wound Healing—Aiming for Perfect Skin Regeneration", Science, 276: 75-81, Apr. 4, 1997.

Stedman "Illustrated Stedman's Medical Dictionary", 5th Unabridged Lawyer's Edition, Jefferson Law Book Company, p. 382, 776, 1982.

Communication Pursuant to Article 94(3) EPC Dated Jul. 17, 2009 From the European Patent Office Re.: Application No. 01996012.9.

International Preliminary Report on Patentability Dated Apr. 18, 2003 From the International Preliminary Examining Authority Re.: Application No. PCT/US01/44923.

Response Dated Nov. 13, 2009 to Communication Pursuant to Article 94(3) EPC of Jul. 17, 2009 From the European Patent Office Re.: Application No. 01996012.9.

Burton "Effect of Topiramate on Attention", Epilepsy Research, 27(1): 29-32, Apr. 1997. Abstract.

Carrel et al. "Growth Hormone Improves Body Composition, Fat Utilization, Physical Strenght and Agility, and Growth in Prader-Willi Syndrome: A Controlled Study", The Journal of Pediatrics, 134(2): 215-221, Feb. 1999. Abstract.

Crawford "An Audit of Topiramate 'Ise in a General Neurology Clinic", Seizure, 7(3): 207-211, Jun. 1998. Abstract.

Davanzo "Open Trial of Lamotrigine in the Treatment of Self-Injurious Behavior in An Adolescent With Profound Mental Retardation", Journal of Child & Adolescent Psychopharmacology, 6(4): 273-279, 1996. Abstract.

Donovan et al. "Divalproex Treatment for Youth With Explosive Temper and Mood Lability: A Double-Blind, Placebo-Controlled Crossover Design", American Journal of Psychiatry, 157(5): 818-820, May 2000.

Emerson et al. "The Prevalence of Challenging Behaviors: A Total Population Study", Research in Developmental Disabilities, 22(1): 77-93, Jan.-Feb. 2001. Abstract.

Faught et al. "Topiramate Placebo-Controlled Dose-Ranging Trial in Refractory Partial Epilepsy Using 200-, 400-, and 600-mg Daily Dosages", Neurology, 46: 1684-1690, 1996. Abstract.

Gerber et al. "Factors Associated With Behavioral and Cognitive Abnormalities in Children Receiving Topiramate", Pediatric Neurology, 22(3): 200-203, Mar. 2000. Abstract.

Glenn et al. "Genomic Imprinting: Potential Function and Mechanisms Revealed by the Prader-Willi and Angelman Syndromes", Molecular Human Reproduction, 3(4): 321-332, 1997.

Ireland "A Descriptive Analysis of Self-Harm Reports Among A Sample of Incarcerated Adolescent Males", Journal of Adolescence, 23: 605-613, 2000.

Jones "Topiramate—Safety and Tolerability", The Canadian Journal of Neurological Sciences, 25(Suppl.3): S13-S15, Aug. 1998. Abstract.

Ko "Under-Diagnosed Psychiatric Syndrome II: Pathologic Skin Picking", Annals of the Academy of Medicine, Singapore, 28(4): 557-559, Jul. 1999. Abstract.

Lindgren et al. "Effects of Growth Hormone Treatment on Growth and Body Composition in Prader-Willi Syndrome: A Preliminary Report. The Swedish National Growth Hormone Advisory Group", Acta Paediatrica Supplement, 423: 60-62, Nov. 1997. Abstract.

Marcotte "Use of Topiramate, A New Anti-Epileptic as a Mood Stabilizer", Journal of Affective Disorders, 50(2-3): 245-251, Sep. 1998. Abstract.

Martin et al. "Clinical Case Conference. Prader-Willi Syndrome", The American Journal of Psychiatry, 155: 1265-1273, Sep. 1998.

Martin et al. "Cognitive Effects of Topiramate, Gabapentin, and Lamotrigine in Healthy Young Adults", Neurology, 52(2): 321-327, Jan. 15, 1999. Abstract.

McElroy et al. "Open-Label Adjunctive Topiramate in the Treatment of Bipolar Disorders", Biological Psychiatry, 47(12): 1025-1033, Jun. 2000. Abstract.

Mikati et al. "Gabapentin in the Treatment of Refractory Partial Epilepsy in Children With Intellectual Disability", Journal of Intellectual Disability Research: JIDR, 42(Suppl.1): 57-62, Dec. 1998. Abstract.

Mitchell et al. "Effects of Antiepileptic Drugs on Reaction Time, Attention, and Impulsivity in Children", Pediatrics, 91(1): 101-105, Jan. 1993. Abstract.

Mitchell et al. "Reaction Time, Attention, and Impulsivity in Epilepsy", Pediatric Neurology, 8(1): 19-24, Jan.-Feb. 1992. Abstract.

Persinger "Subjective Improvement Following Treatment With Carbamazepine (Tegretol) for A Subpopulation of Patients With Traumatic Brain Injuries", Perceptual and Motor Skills, 90(1): 37-40, Feb. 2000. Abstract.

Privitera et al. "Topiramate Placebo-Controlled Dose-Ranging Trial in Refractory Partial Epilepsy Using 600-, 800-, and 1,000-mg Daily Dosages", Neurobiology, 46: 1678-1683, 1996. Absract.

Roach et al. "Carbamazepine Trial for Lesch-Nyhan Self-Mutilation", Journal of Child Neurology, 11(6): 476-478, Nov. 1996. Abstract.

Rosenfeld et al. "Comparison of the Steady-State Pharmacokinetics of Topiramate and Valproate in Patients With Epilepsy During Monotherapy and Concomitant Therapy", Epilepsia, 38(3): 324-333, 1997.

Ruedrich et al. "Effect of Divalproex Sodium on Aggression and Self-Injurious Behaviour in Adults With Intellectual Disability: A Retrospective Review", Journal of Intellectual Disability Research, 43(2): 105-111, Apr. 1999.

Selikowitz et al. "Fenfluramine in Prader-Willi Syndrome: A Double Blind, Placebo Controlled Trial", Archives of Disease in Childhood, 65(1): 112-114, Jan. 1990. Abstract.

Silva et al. "Carbamazepine Use in Children and Adolescents With Features of Attention-Deficit Hyperactivity Disorder: A Meta-Analysis", Journal of the American Academy of Child & Adolescent Psychiatry, 35(3): 352-358, Mar. 1996. Abstract.

Thompson et al. "Effects of Topiramate on Cognitive Function", Journal of Neurology, Neurosurgery and Psychiatry, 69(5): 636-641, Nov. 2000. Abstract.

Wilhelm et al. "Self-Injurious Skin Picking: Clinical Characteristics and Comorbidity", The Journal of Clinical Psychiatry, 60(7): 454-459, Jul. 1999.

Fuziwara et al. "NMDA-Type Glutamate Receptor Is Associated With Cutaneous Barrier Homeostasis", Journal of Investigative Dermatology, 120: 1023-1029, 2003.

Han et al. "Wound Healing Activity of Gamma-Aminobutyric Acid (GABA) in Rats", Journal of Microbiology and Biotechnology, 17(10): 1661-1669, 2007.

Ito et al. GABA-Synthesizing Enzyme, GAD67, From Dermal Fibroblasts: Evidence for A New Skin Function, Biochimica et Biophysica Acta, 1770: 291-296, 2007.

Kelley et al. "Does Gamma-Aminobutyric Acid (GABA) Influence the Development of Chronic Inflammation in Rheumatoid Arthritis?", Journal of Neuroinflammation, 5(1): 1-5, 2008.

International Search Report Dated Sep. 27, 2002 From the International Searching Authority Re.: Application No. PCT/US01/44923.

* cited by examiner

GFV-003
October 30, 2000
25 mg
Patient already showing healing on left arm lesion from decreased skin picking on low dose topiramate for 1 week. This lesion had been wet and oozing 1 week prior.

FIG. 9A

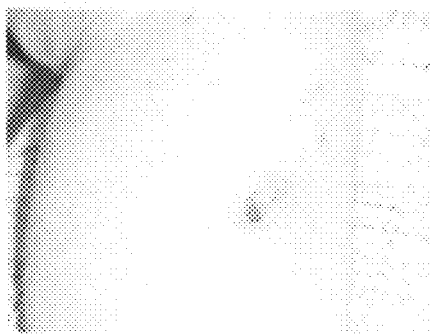

GFV-003
November 6, 2000
50 mg
Patient continues showing healing on left arm lesion from decreased skin picking.

FIG. 9B

GFV-003
November 15, 2000
75 mg
Patient continuing to show healing on left arm lesion from decreased skin picking on topiramate as the close up to the lesion shows.

FIG. 9C

GFV-003
November 21, 2000
100 mg
Patient with completely healed over lesion on left arm from decreased skin picking on topiramate.

FIG. 9D

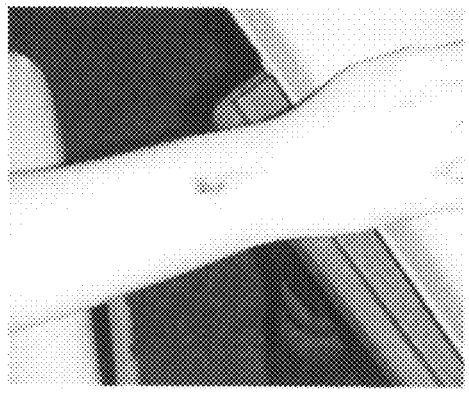

FIG. 10A

MJG-001
October 27, 2000
75 mg
Patient's right arm skin lesion which had been completely open and wet approximately 1 ½ months earlier shows healing with her decreased skin picking on topiramate

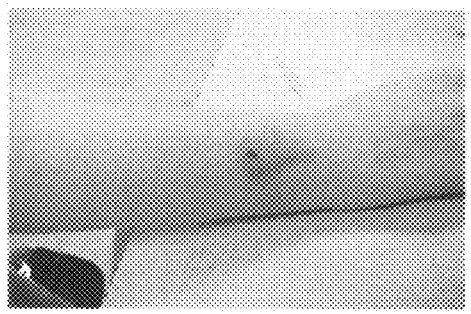

FIG. 10B

MJG-001
November 15, 2000
125 mg
Patient's skin is continuing to heal with decreased skin picking on topiramate.

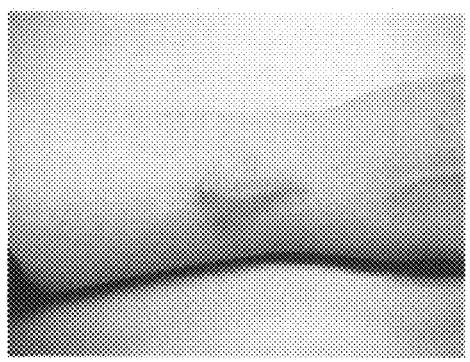

FIG. 10C

MJG-001
November 20, 2000
125 mg
Patient's skin is showing significant healing with decreased skin picking on topiramate for approximately 2 months.

\* lesions smaller than previous ones and appeared to result after insect bites

TREATMENTS FOR WOUND HEALING

CROSS-REFERENCE TO RELATED APPLICATIONS

This application is a continuation of U.S. patent application Ser. No. 11/013,259, filed Dec. 15, 2004, which is a continuation of U.S. patent application Ser. No. 09/997,447, filed Nov. 30, 2001, which claims the benefit of U.S. Provisional Application No. 60/250,113, filed Nov. 30, 2000, which are hereby incorporated by reference herein in their entireties, including any figures, tables, or drawings.

BACKGROUND OF THE INVENTION

As many as one-third of the approximate 3,000 known genetic disorders are believed to have important neurological involvement. Individually, most genetic disorders are of low incidence in the general population; however, collectively they represent an enormous burden on affected individuals, their families, and society. Many neurogenetic disorders manifest themselves early in life leading to either a premature death or to lifelong disability with significant attendant psychological and economic hardships.

Examples of these types of disorders include: (1) Hereditary ataxias and related disorders such as Friedreich ataxia, ataxia telangiectasia, olivopontine cerebellar degeneration, Ramsay Hunt syndrome, abetalipoproteinemia, Machado-Joseph disease, and familial spastic paraparesis; (2) Movement disorders such as Juvenile Huntington disease, the dystonias including blepharospasm and spasmodic torticolis, tremor, myoclonus, and Hallervorden-Spatz disease; (3) Phakomatoses, or neurocutaneous syndromes such as neurofibromatosis, tuberous sclerosis, Sturge-Weber, and Von Hippel-Landau disease; (4) Mitochondrial encephalomyopathies such as the MELAS syndrome, Kearns-Sayre, and Leigh disease; (5) Hereditary disorders of nerve and muscle such as infantile spinal muscular atrophy, Charcot-Marie-Tooth disease, hereditary sensory and autonomic neuropathies, genetic myasthenic syndromes, metabolic myopathies, muscular dystrophies, and myotonias.

There are numerous other neurological disorders that are also believed to result from genetic abnormalities such as the Laurence-Moon-Bardet-Biedl, Aicardi, Sjogren-Larsson, Prader-Willi and Angelman syndromes.

In addition to those diseases that have a recognizable pattern of inheritance, there are many other neurological disorders that seem to have, in some cases, a familial basis. These may well represent neurogenetic disorders with multifactorial etiology. Such diseases can be as diverse as disorders of defective cellular migration (such as lissencephaly, heterotopias), neural tube defects, congenital hydrocephalus, myoclonic epilepsy, attention deficit hyperactivity disorder (ADHD), and narcolepsy.

It is estimated that ADHD affects about 4% to 6% of the U.S. population. ADHD is not limited to children and is a chronic lifetime disease. Approximately one-half to two-thirds of children with ADHD will continue to have significant problems in adulthood and experience difficulties which impact employment, familial, and social relationships.

According to the DSM-IV (the Diagnostic and Statistical Manual of Mental Disorders, Fourth Edition) some common symptoms of ADHD include: (1) often fails to give close attention to details or makes careless mistakes; (2) often has difficulty sustaining attention to tasks; (3) often does not seem to listen when spoken to directly; (4) often fails to follow instructions carefully and completely; (5) losing or forgetting important things; (6) feeling restless, often fidgeting with hands or feet, or squirming; (7) running or climbing excessively; (8) often talks excessively; (9) often blurts out answers before hearing the whole question; and (10) often has difficulty awaiting turn. It should be kept in mind that the exact nature and severity of ADHD symptoms varies from person to person however. Approximately one-third of people with ADHD do not have the hyperactive or overactive behavior component.

To meet diagnostic criteria, these behaviors must be excessive, long-term, and pervasive. The behaviors must appear before age 7, and continue for at least 6 months. A crucial element requires that the behaviors must create a real handicap in at least two areas of a person's life, such as school, home, work, or social settings. These criteria set ADHD apart from the "normal" distractibility and impulsive behavior of childhood, or the effects of the hectic and overstressed lifestyle prevalent in our society.

There are no reports in the literature of topiramate specifically used to treat deficits in attention and concentration. Carbamazepine (Tegretol) has been reported to be useful for the treatment of patients experiencing sudden confusion and depression. Within weeks of initiating treatment, the patients experienced fewer incidences of sudden confusion and depression, and an increase in attention and focus. Persinger, M. A., "Subjective improvement following treatment with carbamazepine (Tegretol) for a subpopulation of patients with traumatic brain injuries", *Percept Mot Skills* 90:37-40 (2000). Carbamazepine has also been shown to be effective in treating children with features of ADHD. Silva, R. R.; Munoz, D. M.; Alpert, M., "Carbamazepine use in children and adolescents with features of attention-deficit hyperactivity disorder: a meta-analysis", *J Am Acad Child Adolesc Psychiatry* 35:352-358 (1996). In some patients, with or without intellectual disability, being treated for refractory partial epilepsy, gabapentin is an equally effective add-on medication. Mikati, M. A.; Choueri, R.; Khurana, D. S.; et al., "Gabapentin in the treatment of refractory partial epilepsy in children with intellectual disability", *J Intellect Disabil Res* 42:57-62 (suppl. 1, 1998). Three dementia patients are noted in the literature to have received topiramate in a retrospective chart review of 58 consecutive psychiatric patients receiving topiramate. Marcotte, D., "Use of topiramate, a new anti-epileptic as a mood stabilizer", *J Affect Disorder* 50:245-251 (1998). "Improvement" was rated by a Likert scale from 'worse,' to 'no change,' to 'minimally improved,' to 'moderately improved,' to 'markedly improved.' The three patients with dementia are described to have 'moderate' or 'marked' improvement when on topiramate. The author of this chart review hypothesized that topiramate may have some antipsychotic effect.

While there have been no reported efforts to use topiramate for the treatment of impulsivity, there have been a limited number of publications reporting the effects of anti-convulsant treatment on impulsivity (or measures of impulsivity). These references tend to show no change or worsening of impulsivity with anti-convulsant treatment. For example, one large study showed no overall effect on measures of impulsivity of anti-convulsant medication in epileptic children (Mitchell, W. G.; Zhou, Y.; Chavez, J. M.; Guzman, B. L., "Reaction time, attention, and impulsivity in epilepsy", *Pediatr Neurol* 8:19-24 (1992)) and another large study showed, at higher total serum levels of anti-convulsant medication in children with epilepsy, more impulsive errors on complex reaction time testing (Mitchell, W. G.; Zhou. Y.; Chavez, J. M.; Guzman, B. L., "Effects of anti-epileptic drugs on reaction time, attention, and impulsivity in children", *Pediatrics*

91:101-105 (1993)). It is notable that both of these studies focused on children with epilepsy.

A case report from 1987 described carbamazepine being useful for intermittent explosive disorder in a patient with Prader-Willi Syndrome (Gupta, B. K.; Fish, D. N.; Yerevanian, B. I., "Carbamazepine for intermittent explosive disorder in a Prader-Willi syndrome patient", *J Clin Psychiatry* 48:423 (1987)). Carbamazepine has also been reported useful in the treatment of pathological gambling (Haller, R.; Hinterhuber, H., "Treatment of pathological gambling with carbamazepine", *Pharmacopsychiatry* 27:129 (1994)). There are also reports in the literature of divalproex being effective for explosive mood and mood lability (Donovan, S. J.; Stewart, J. W.; Nunes, E. V.; Quitkin, F. M.; Parides, M.; Daniel, W.; Susser, Klein D. F., "Divalproex treatment for youth with explosive temper and mood lability: a double-blind, placebo-controlled crossover design", *Am J Psychiatry* 157:818-820 (2000)) and for a patient with kleptomania and mixed mania (Kmetz, G. F.; McElroy, S. L.; Collin, D. J., "Response of kleptomania and mixed mania to valproate", *Am J Psychiatry* 154:580-581 (1997)).

Prader-Willi Syndrome (PWS) is a neurogenetic multisystem disorder characterized by infantile hypotonia, mental retardation, short stature, hypogonadism, dysmorphic features, and hyperphagia with a high risk of obesity. Also very common in PWS are behavioral and psychiatric manifestations. These include self-injury (e.g. gouging, nail biting, and skin picking), explosive outbursts, oppositional behavior, obsessive ruminations, and compulsive behaviors including hoarding, counting, and arranging. PWS is typically a sporadic condition, which usually results from a deletion in chromosome 15q11-q13 or maternal uniparental disomy of chromosome 15. Glenn, C. G.; Driscoll, D. J.; Thomas, P. Y.; Nicholls, R. D., "Genomic imprinting: potential function and mechanisms revealed by the Prader-Willi and Angelman syndromes", *Mol Hum Reprod* 3:321-332 (1997).

PWS is also a relatively common genetic condition with an estimated prevalence of approximately 1/10,000 to 1/25,000. Glenn, C. G.; Driscoll, D. J.; Thomas, P. Y.; Nicholls, R. D., "Genomic imprinting: potential function and mechanisms revealed by the Prader-Willi and Angelman syndromes", *Mol Hum Reprod* 3:321-332 (1997). It was first described in 1956 (Prader, A.; Labhart, A.; Willi, H., "Ein Syndrome von adipositas, Kleinwuchs, Kryptorchismus und Oligophrenic nach myoteniertigem zusland in neugeborenanalter", *Schwiez Med Wschr* 86:1260-1 (1956), and the physical problems (such as the obesity related cardiovascular diseases, diabetes mellitus, etc.) and behavioral problems result in the major causes of morbidity and mortality. Martin, A.; Matthew, S.; Koenig, K.; et al., "Prader-Willi syndrome", *Am J Psychiatry* 155:1265-1273 (1998).

Treatment for the physical, behavioral, and psychological problems associated with PWS is complex. The mainstay of treatment for behavioral problems including hyperphagia is behavioral modification including strategies such as token economies or star systems. Dykens, E. M.; Hodapp, R. M., "Treatment issues in genetic mental retardation syndromes", *Professional Psychology: Research and Practice* 28:263-270 (1997). Additionally, medication management of individuals with PWS has been demonstrated to have benefit. Growth hormone therapy in children with PWS can increase muscle tone and enhance growth. Carrel, A. L.; Myers, S. C.; Whitman, B. Y.; et al., "Growth hormone improves body composition, fat utilization, physical strength and agility, and growth in Prader-Willi syndrome: A controlled study", *J Pediatr* 134:215-221 (1999); Lindgren, A. C.; Hagenas, L.; Muller, J.; et al., "Effects of growth hormone treatment on growth and body composition in Prader-Willi syndrome: a preliminary report", *The Swedish National Growth Hormone Advisory Group. Acta Paediatr Suppl* 423:60-62 (1997). Therefore, growth hormone can help to normalize body habitus. Martin, A.; Matthew, S.; Koenig, K.; et al., "Prader-Willi syndrome", *Am J Psychiatry* 155:1265-1273 (1998); Carrel, A. L.; Myers, S. C.; Whitman, B. Y.; et al., "Growth hormone improves body composition, fat utilization, physical strength and agility, and growth in Prader-Willi syndrome: A controlled study", *J Pediatr* 134:215-221 (1999); Lindgren, A. C.; Hagenas, L.; Muller, J.; et al., "Effects of growth hormone treatment on growth and body composition in Prader-Willi syndrome: a preliminary report", *The Swedish National Growth Hormone Advisory Group. Acta Paediatr Suppl* 423: 60-62 (1997). In terms of obesity, the anorectic fenfluramine was shown to be helpful for weight loss and aggressive behavior in PWS utilizing a double-blind placebo-controlled trial. Selikowitz, M.; Sunman, J.; Pendergast, A.; et al., "Fenfluramine in Prader-Willi syndrome: a double-blind, placebo controlled trial", *Arch Dis Childhood* 65:112-114 (1990). Unfortunately due to cardiovascular consequences, fenfluramine is not now currently available. There are few studies of anorectic agents in PWS and anecdotal reports have been discouraging in terms of their benefits. Martin, A.; Matthew, S.; Koenig, K.; et al., "Prader-Willi syndrome", *Am J Psychiatry* 155:1265-1273 (1998).

Pathological skin picking (PSP) is a severe and chronic psychiatric and dermatologic problem with an average age of onset around 15 years of age and mean duration of illness of 21 years. Keuthen, W. S.; Deckersbach, T.; Engelhard, I. M.; et al., "Self-injurious skin picking: clinical characteristics and comorbidity", *J Clin Psychiatry* 60:454-459 (1999). PSP can lead to significant suffering, dysfunction, and disfigurement. Ko, S. M., "Under-diagnosed psychiatric syndrome II: Pathologic skin picking", *Ann Acad Med Singapore* 28:557-559 (1999). Furthermore, there is often psychiatric comorbidity. Keuthen, W. S.; Deckersbach, T.; Engelhard, I. M.; et al., "Self-injurious skin picking: clinical characteristics and comorbidity", *J Clin Psychiatry* 60:454-459 (1999). PSP is often considered an obsessive compulsive spectrum disorder (Goldsmith, T. D.; Shapira, N. A.; Phillips, K. A.; et al., "Obsessive Compulsive Spectrum Disorders"; in: Swinson, R. P.; Antony, M. M.; Rachman, S.; Richter, M. A. (Eds)., *Obsessive-Compulsive Disorder. Theory, Research, and Treatment*, Guilford Publications, New York, pp. 397-425 (1998)) and, as such, there are several reports of serotonin receptor inhibitors (SSRI) medication being helpful. Ko, S. M., "Under-diagnosed psychiatric syndrome II: Pathologic skin picking", *Ann Acad Med Singapore* 28:557-559 (1999).

The literature points to topiramate having a negative impact on cognitive functioning including impaired concentration, attention, memory, slowed thinking, word finding, and verbal fluency. Thompson, P. J.; Baxendale, S. A.; Duncan, J. S.; et al.; "Effects of topiramate on cognitive function", *J Neurol Neurosurg Psychiatry* 69:636-641 (2000); Privitera, M.; Fincham, R.; Penry, J.; et al., "Topiramate placebo-controlled dose-ranging trial in refractory partial epilepsy using 600-, 800-, and 1,000-mg daily dosages", *Topiramate YE Study Group. Neurology* 46:1678-1683 (1996); Crawford, P., "An audit of topiramate use in a general neurology clinic", *Seizure* 7:207-211 (1998); Jones, M. W., "Topiramate— safety and tolerability", *Can J Neurol Sci* 25:S13-15 (1998); Burton, L. A.; Harden, C., "Effect of topiramate on attention", *Epilepsy Res* 27:29-32 (1997); Martin, R.; Kuzniecky, R.; Ho, S. "Cognitive effects of topiramate, gabapentin, and lamotrigine in healthy young adults", *Neurology* 52:321 (1999); Fraught, E.; Wilder, B. J.; Ramsay, R. E.; et al., "Topiramate placebo-controlled dose-ranging trial in refractory partial epilepsy using 200-, 400-, and 600-mg daily dosages," *Neurology* 46:1684-1690 (1996); and Rosenfeld, W. E.; Liao, S.; Kramer, L. D.; et al., "Comparison of the steady-state pharmacokinetics of topiramate and valproate in patients with epilepsy during monotherapy and concomitant therapy", *Epilelpsia* 38:324-333 (1997). A few studies have systematically looked at cognitive changes using neuropsychological testing. In one study (Burton, L. A.; Harden, C., "Effect of topiramate on attention", *Epilepsy Res* 27:29-32 (1997)), 10 adult patients with epilepsy were evaluated weekly for up to 13 weeks via a digit span test. In 4 patients, there was an inverse correlation between topiramate does and test performance. In another study, healthy volunteers were treated with topiramate, gabapentin, or lamotrigine for 4 weeks. Impaired cognitive functioning (attention and word fluency) was seen in the topiramate treated subjects and not in gabapentin or lamotrigine in these healthy young adults. Martin, R.; Kuzniecky, R.; Ho, S. "Cognitive effects of topiramate, gabapentin, and lamotrigine in healthy young adults", *Neurology* 52:321 (1999). Finally, in a recent study of 18 epilepsy patients treated with topiramate and receiving repeat neuropsychological assessments, patients on topiramate showed significant deterioration in many cognitive domains, including verbal IQ, verbal fluency, and verbal learning. Thompson, P. J.; Baxendale, S. A.; Duncan, J. S.; et al.; "Effects of topiramate on cognitive function", *J Neurol Neurosurg Psychiatry* 69:636-641 (2000). Improvement in verbal fluency, verbal learning, and digit span increased in patients where topiramate was withdrawn or reduced.

The subject invention has, surprisingly, found improvements in impulsivity control, without negative effects on attention and concentration, in patients treated with topiramate. These observations are unexpected and novel.

BRIEF SUMMARY OF THE INVENTION

The subject invention provides methods and compositions for the treatment of neurogenetic disorders, particularly DSM-IV impulse control disorders such as intermittent explosive disorder, kleptomania, pyromania, pathologic gambling, trichotillomania, and other impulse control disorders such as compulsive buying and problematic Internet use. In a preferred embodiment, the subject invention provides methods for treating or controlling symptoms associated with ADHD or PWS comprising the administration of therapeutically effective amounts of compositions containing compounds of the formulas I-V. In another embodiment, the subject invention provides for methods of promoting wound healing comprising the administration of a therapeutically effective amount of a composition comprising the compounds of formulas I-V. Compositions are administered to a wound site via a salve, ointment, or as a component of a bandage or bioadhesive applied to the site of injury. The invention also provides therapeutically effective compositions comprising one or more of the compounds of formulas I-V.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIGS. 9A-D and 10A-C depict the progression of wound healing in patients treated with topiramate.

DETAILED DISCLOSURE OF THE INVENTION

Figure 1:
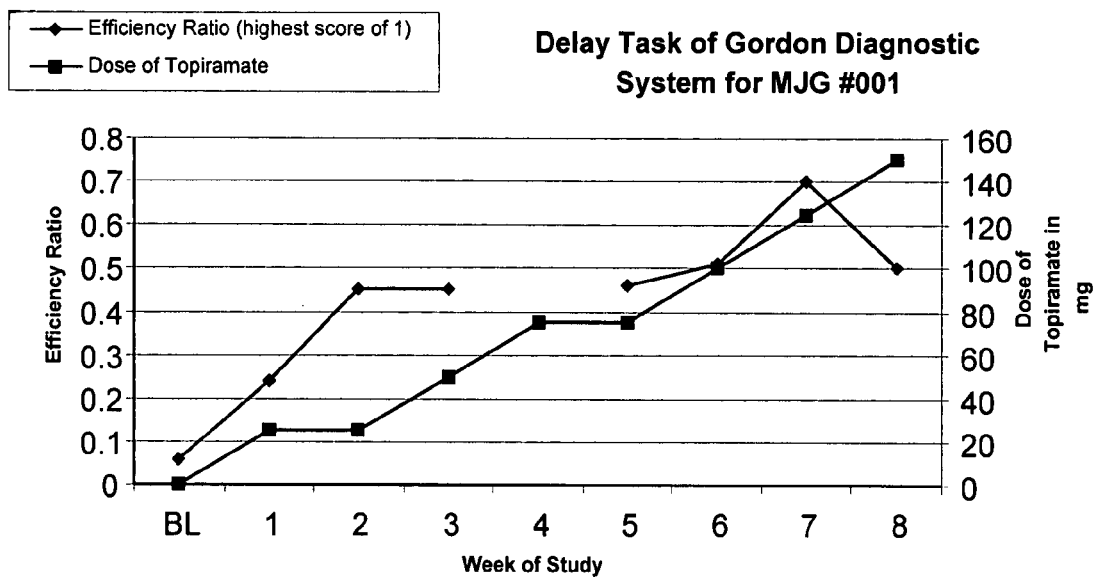
FIGS. 1, 3, 5, and 7 depict the efficiency ratios of patients treated with topiramate as measured by the Delay Task of the Gordon Diagnostic.
Figure 2:
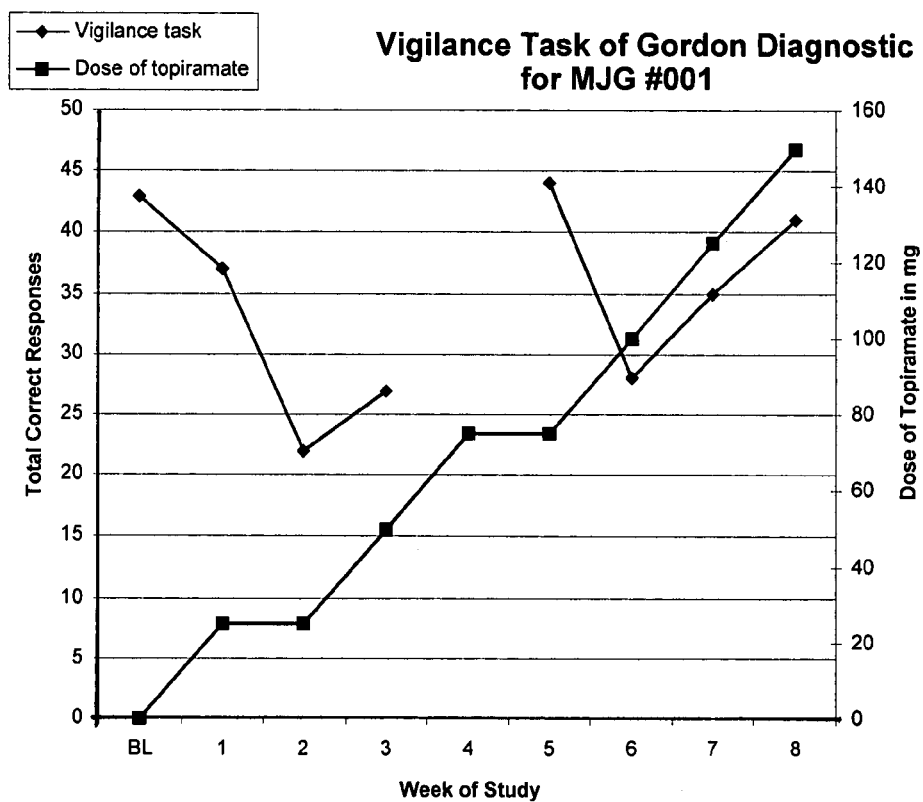
FIGS. 2, 4, 6, and 8 depict the total correct responses of patients treated with topiramate as measured by the Vigilance Task of the Gordon Diagnostic.
Figure 3:
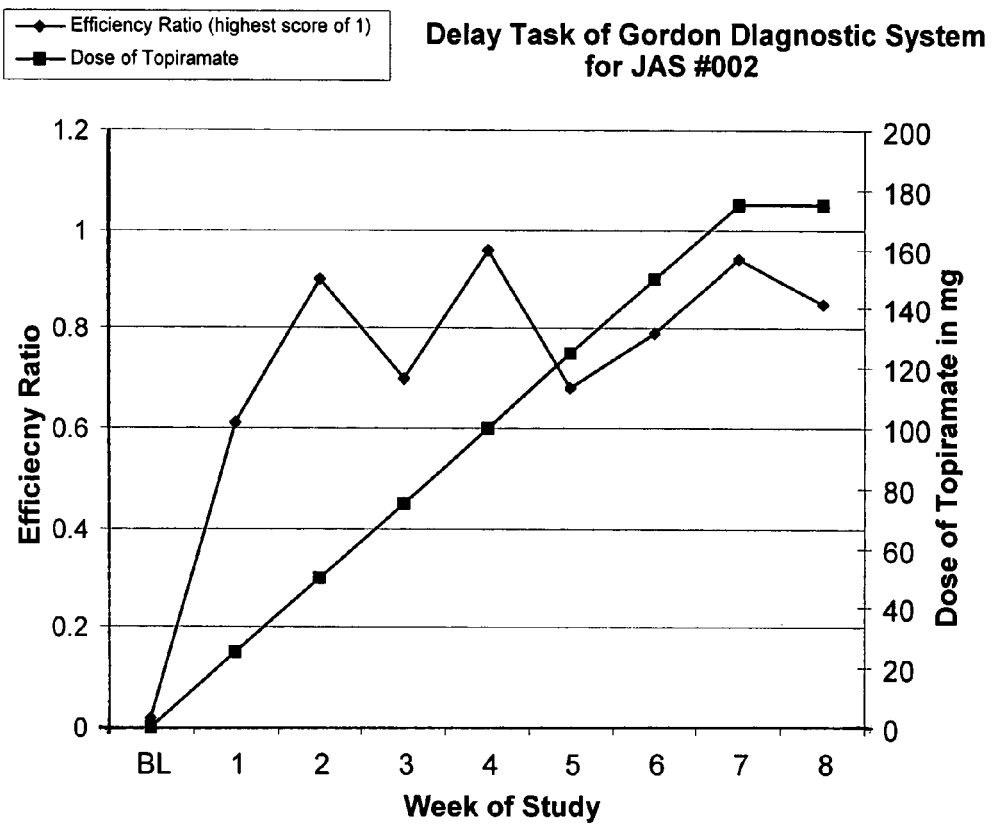
Figure 4:
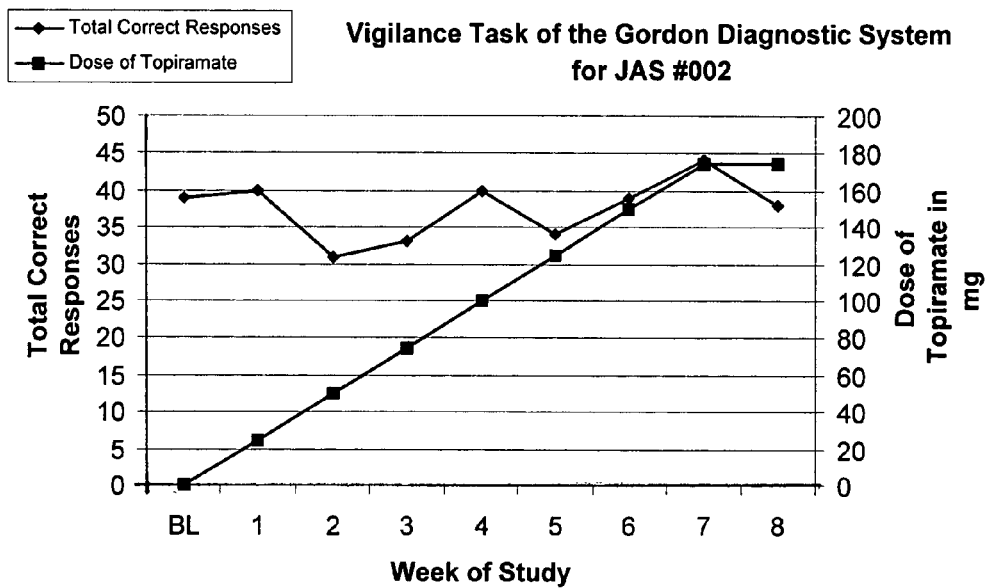
Figure 5:
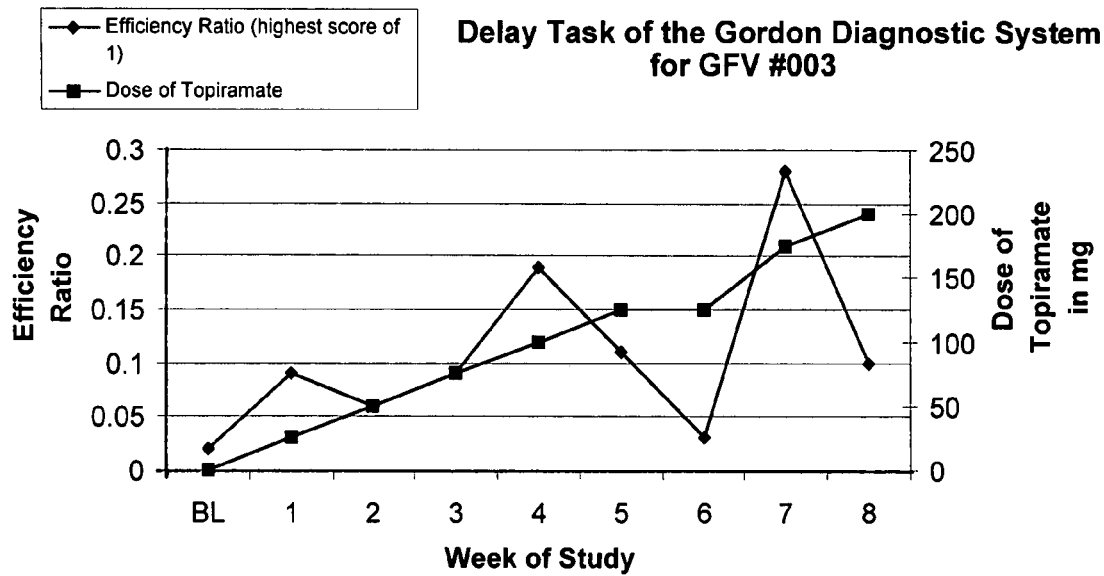
Figure 6:
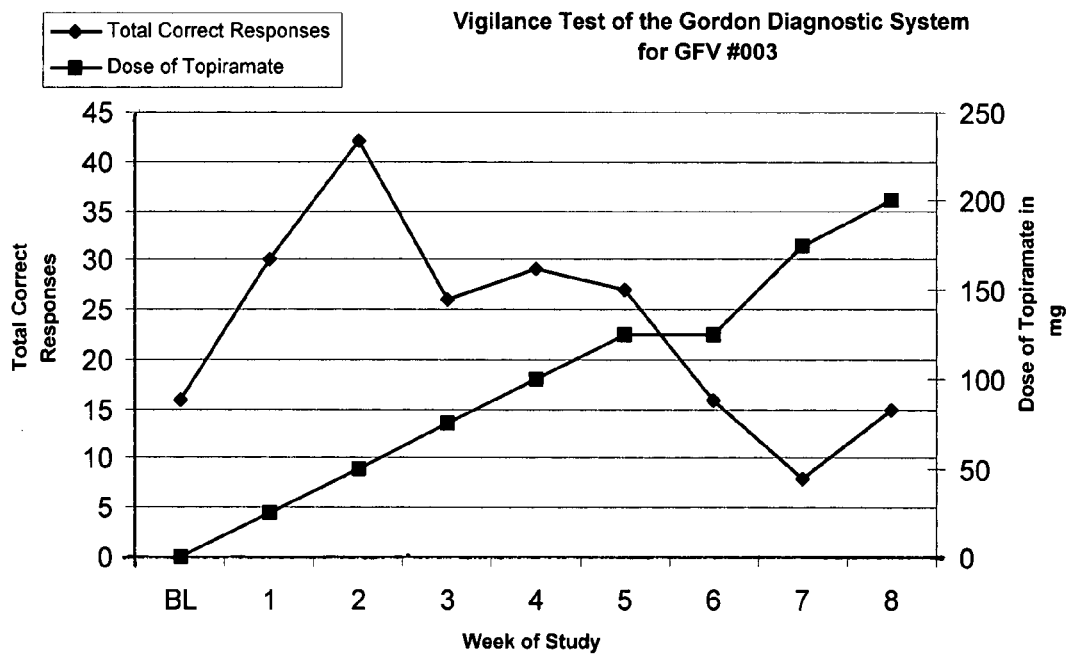
Figure 7:
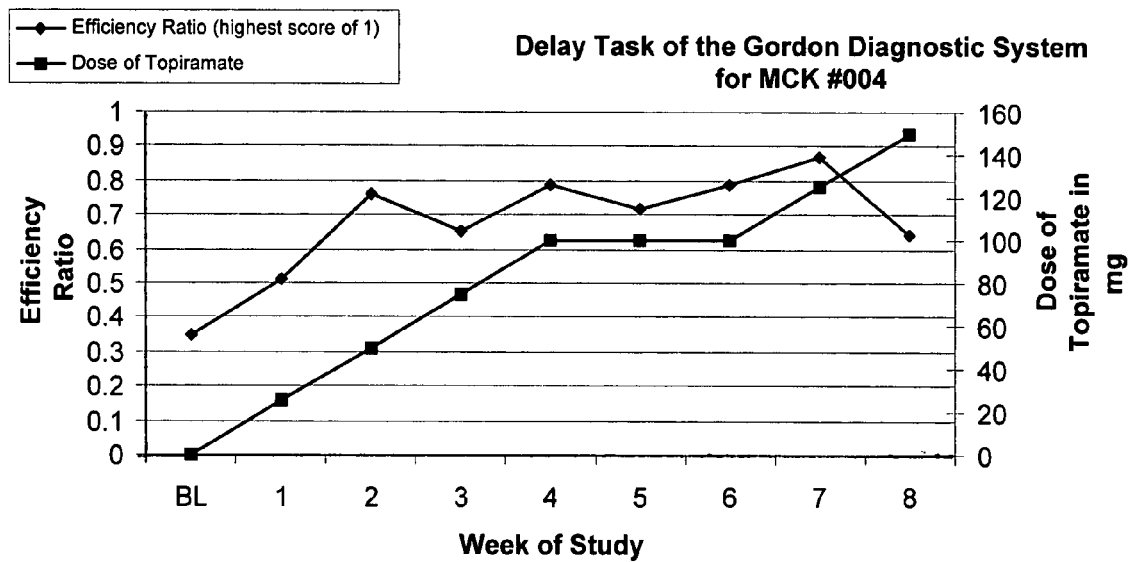
Figure 8:
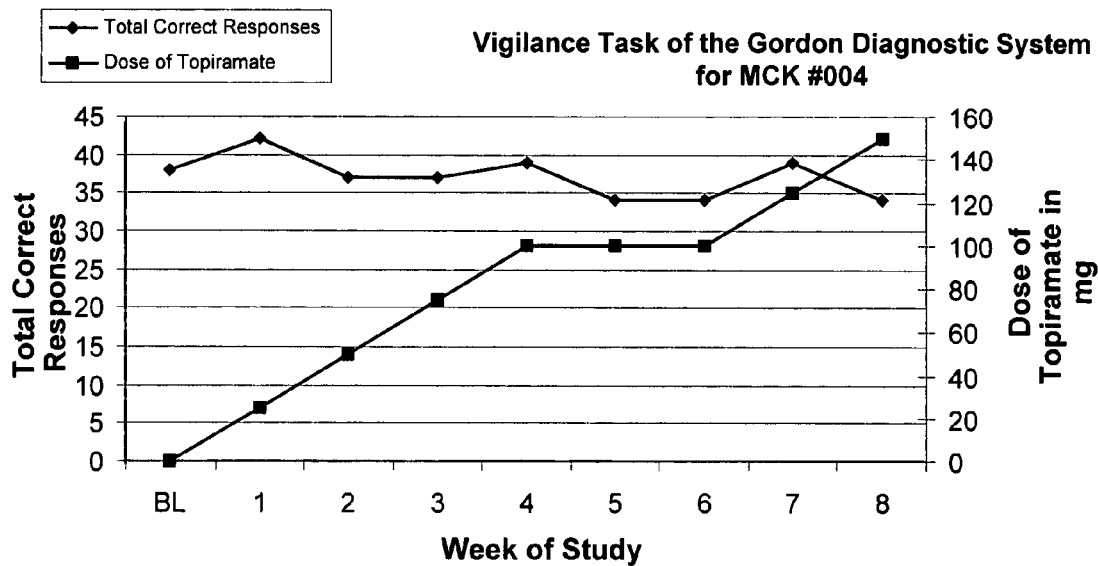
Figure 11A:
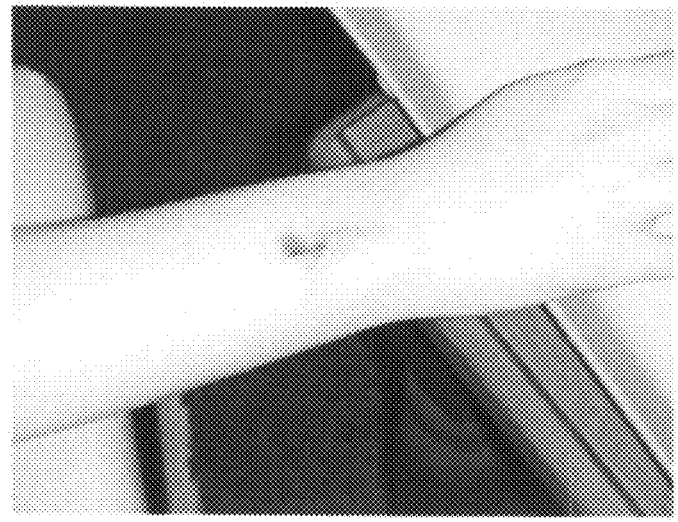
FIGS. 11A-B: Photographs of improvement in wound healing for Ms. A on topiramate (75 mg/day) at week 4 (FIG. 11A) and 150 mg/day topiramate at week 8 (FIG. 11B).
Figure 11B:
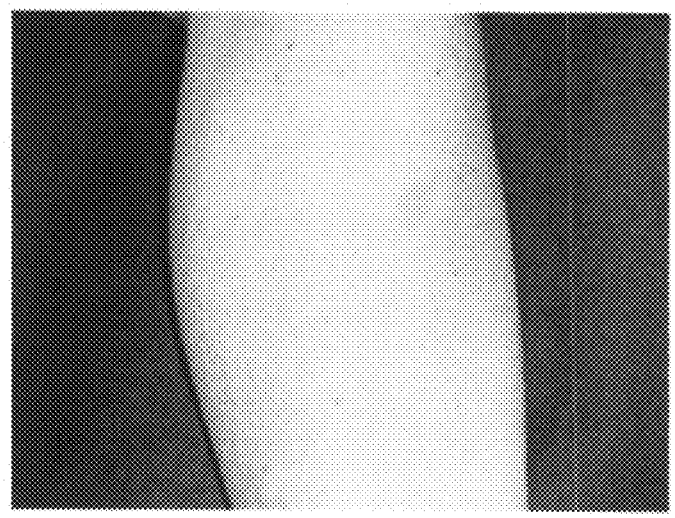
Figure 12A:
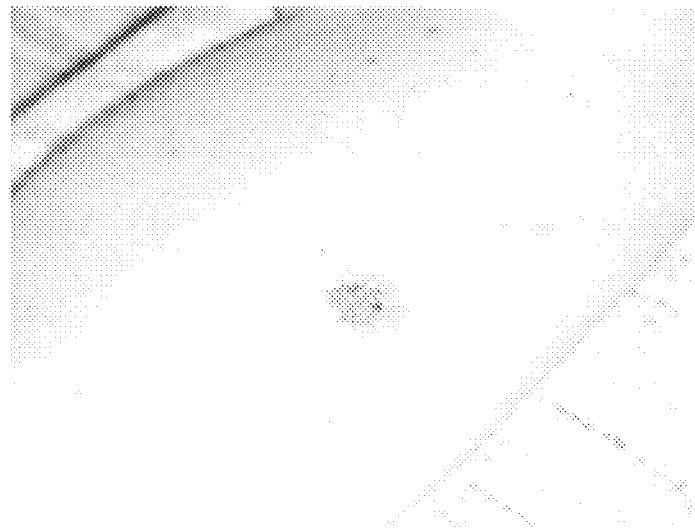
FIGS. 12A-B: Photographs of improvement for Mr. B. Mr. B. on 25 mg/day topiramate (FIG. 12A), Week 1; Mr. B. on 200 mg/day topiramate (FIG. 12B), Week 8.
Figure 12B:

The subject invention provides methods and compositions for the treatment of neurogenetic disorders, particularly DSM-IV impulse control disorders such as intermittent explosive disorder, kleptomania, pyromania, pathologic gambling, trichotillomania, and other impulse control disorders such as compulsive buying and problematic Internet use. In a preferred embodiment, an individual is treated in methods comprising the administration of therapeutically effective amounts of compositions comprising compounds selected from the group consisting of formulas I-V. In one embodiment, therapeutically effective amounts of topiramate are administered to individuals topically or orally. In another embodiment, compositions comprising one or more of the compounds disclosed in formulas I-V are administered for the control or treatment neurogenetic disorders. In preferred embodiments the neurogenetic disorders include PWS and ADHD.

Thus, the subject invention provides methods and compositions for the treatment or control of ADHD or PWS. In one embodiment, the subject invention provides methods for controlling symptoms associated with ADHD or PWS comprising the administration of therapeutically effective amounts of compositions containing compounds of the formulas I-V. One embodiment of the invention provides therapeutically effective compositions comprising one or more of the compounds of formulas I-V and acceptable carriers.

In another embodiment, the subject invention provides methods of promoting wound healing comprising the administration of a therapeutically effective amount of a composition comprising the compounds of formulas I-V to an individual having a wound. In one embodiment, compositions are topically administered to a wound. The compositions may take the form of a salve, ointment, or aerosol applied to the site of injury. Alternatively, the compositions may be administered to the wound site as a component of a bandage or transdermal patch. In these instances, the compositions may be an integral component of the bandage or transdermal patch and are thereby applied to the wound site. In another embodiment, therapeutically effective amounts of the compounds comprising formulas I-V are incorporated into bioadhesive compositions useful in wound closure. In yet another embodiment, therapeutically effective amounts compositions comprising the compounds of formulas I-V are administered orally.

As the subject invention provides methods of promoting wound healing or controlling impulsive behavior in an individual, the subject invention provides methods having both human and veterinary utility. The term "individual" includes animals of avian, mammalian, or reptilian origin. Mammalian species which benefit from the disclosed methods include, and are not limited to, apes, chimpanzees, orangutans, humans, monkeys; domesticated animals (pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, giant pandas, hyena, seals, sea lions, and elephant seals. Reptiles include, and are not limited to, alligators, crocodiles, turtles, tortoises, snakes, iguanas, and/or other lizards. Avian species include, and are not limited to, chickens, turkeys, pigeons, quail, parrots, macaws, dove, Guinea hens, lovebirds, parakeets, flamingos, eagles, hawks, falcons, condor, ostriches, peacocks, ducks, and swans. Therefore, the subject invention provides methods of controlling the impulse of an individual to scratch, pick, lick, or otherwise cause self-injury by repeated mechanical irritation of an injured area.

Bandages and wound dressings incorporating materials to promote wound healing are well known in the art (see, for example, U.S. Pat. Nos. 6,143,037; 6,142,982; 6,136,341; 6,132,759; 6,124,273; 6,096,709; 6,093,388; 6,087,549; 6,051,249; 6,033,684; 6,025,150; 6,022,556; 5,998,692; 5,989,577; 5,981,606; 5,977,428; RE36,370; 5,972,332; 5,968,001; 5,960,795; 5,955,430; 5,914,125; 5,902,600; 5,897,516; 5,876,743; 5,874,479; 5,863,938; 5,856,364; 5,856,245; 5,834,432; 5,807,341; 5,807,300; 5,804,213; 5,780,048; 5,759,570; 5,735,812; 5,716,935; 5,716,337; 5,713,842; 5,707,647; 5,705,477; 5,692,302; 5,685,834; 5,674,912; 5,667,501; 5,663,208; 5,662,924; 5,662,904; 5,658,957; 5,658,956; 5,652,274; 5,648,380; 5,646,190; 5,641,814; 5,633,285; 5,632,727; 5,629,292; 5,614,561; 5,610,148; 5,603,946; 5,602,183; 5,578,022; 5,571,521; 5,525,335; 5,522,794; 5,520,926; 5,519,020; 5,512,291; 5,512,041; 5,507,775; 5,578,310, each of which is incorporated by reference in its entirety).

Bioadhesives incorporating materials to promote wound healing are well known in the art (see, for example, U.S. Pat. Nos. 5,981,606; 5,874,479; 5,863,938; 5,856,364; 5,692,302; 5,674,912; 5,663,208; 5,658,957; 5,658,956; 5,652,274; 5,648,380; 5,646,190; 5,641,814; 5,633,285; 5,631,019; 5,614,561; 5,602,183; 5,578,310, each of which is incorporated by reference in its entirety).

Compounds of formulas I-V are anti-epileptic compounds, which are highly effective anti-convulsants. The compounds useful in the practice of the instant invention include the individual isomers, analogs, and homologs of the disclosed anti-convulsant compounds. Racemic mixtures, as well as the isolated enantiomeric forms, of the compounds can also be used in the practice of the subject invention.

In addition, the compounds useful for the practice of the subject invention include pharmaceutically acceptable salts, for example; alkali metal salts, such as sodium or potassium, ammonium salts, dialkyammonium salts, trialkylammonium salts, tetraalkylammonium salts, and tromethamine salts. Hydrates and other solvates of the compounds are also included within the scope of the compounds useful in the practice of this invention.

One such compound is taught and disclosed in U.S. Pat. No. 4,513,006, hereby incorporated by reference in its entirety. 2,3:4,5-bis-O-(1-methylethylidene)-β-D-fructopyranose sulfamate, known as topiramate, has been demonstrated in clinical trials of human epilepsy to be effective as adjunctive therapy or as monotherapy in treating simple and complex partial seizures and secondarily generalized seizures. Other useful compounds include those described by formula I, including (tetrahydro-2H-pyran-2-yl)methane sulfamate, and 2,3:4,5-bis-O-(1-methylethylidene)-β-D-fructopyranose methylsulfamate

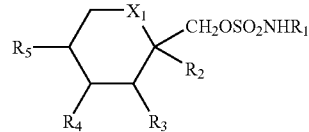

(Formula I)

wherein
$X_1$ is $CH_2$ or oxygen;
$R_1$ is hydrogen or alkyl; and
$R_2$, $R_3$, $R_4$, and $R_5$ are independently hydrogen or lower alkyl and, when $X_1$ is $CH_2$, $R_4$, and $R_5$ may be alkene groups joined to form a benzene ring and, when $X_1$ is oxygen, $R_2$ and $R_3$ and/or $R_4$ and $R_5$ together may be a methylenedioxy group of the following formula:

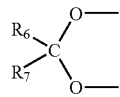

wherein $R_6$ and $R_7$ are the same or different and are hydrogen, lower alkyl or are alkyl and are joined to form a cyclopentyl or cyclohexyl ring.

For compounds of formula I, $R_1$ may be hydrogen or an alkyl of about 1 to 4 carbons, such as methyl, ethyl, and isopropyl. Alkyl includes straight and branched chain alkyl. For compounds of formula I, Alkyl groups for $R_2$, $R_3$, $R_4$, $R_5$, $R_6$, and $R_7$ are of about 1 to 3 carbons and include methyl, ethyl, isopropyl and N-propyl.

When $X_1$ is $CH_2$, $R_4$ and $R_5$ may combine to form a benzene ring fused to the 6-membered $X_1$-containing ring, i.e., $R_4$ and $R_5$ are defined by the alkatrienyl group =CH—CH=CH—CH=.

In one embodiment, $X_1$ is oxygen and both $R_2$ and $R_3$ and $R_4$ and $R_5$ together are methylenedioxy groups of the formula wherein $R_6$ and $R_7$ are both hydrogen, both alkyl or combine to form a spiro cyclopentyl or cyclohexyl ring, in particularly where $R_6$ and $R_7$ are both alkyl such as methyl. In another embodiment, $X_1$ is $CH_2$ and $R_4$ and $R_5$ are joined to form a benzene ring. Another embodiment provides compounds of formula (I) wherein both $R_2$ and $R_3$ are hydrogen.

Other compounds (formulas II-VI) and compositions useful in the practice of the subject invention may be found in the teachings of U.S. Pat. Nos. 5,384,327, 5,498,629, 5,654,461, 5,892,088, and 6,071,537, each of which is incorporated by reference in their entireties.

These compounds include those provided by the structure:

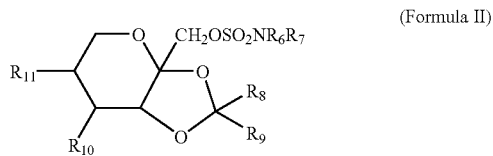
(Formula II)

wherein $R_6$ and $R_7$ may be the same or different and are selected from any of hydrogen or $C_1$ to $C_4$ alkyl. In one embodiment, $R_6$ and $R_7$ are each hydrogen.

$R_8$ and $R_9$ may be the same or different and are selected from any of hydrogen or $C_1$ to $C_4$ alkyl. In one embodiment, $R_8$ and $R_9$ are each $C_1$ to $C_4$ alkyl.

$R_{10}$ and $R_{11}$ may be the same or different and are selected from any of azido, halogen, hydroxyl, sulfamoyl ($H_2NSO_2O$), $C_1$ to $C_4$ alkoxy, $C_1$ to $C_4$ alkyl thiocarbonate (RSC(O)O), $C_1$ to $C_4$ alkyl carbonate (ROC(O)O), or $C_1$ to $C_4$ alkyl carboxylate (RC(O)O), wherein R is $C_1$ to $C_4$ alkyl. In one embodiment, $R_{10}$ and $R_{11}$ are selected from any of $C_1$-$C_4$ alkyl thiocarbonate, halogen or hydroxyl.

For compounds of formula II, the terms alkyl and alkoxy include straight and branched chains. For example, alkyl radicals include methyl, ethyl, propyl, isopropyl, n-butyl, isobutyl, and t-butyl. Halogen includes bromine, chlorine, fluoride and iodine.

Preferred compounds of the formula (II) are those wherein the pyran ring is in the L-sorbopyranose absolute configuration. Particularly preferred compounds of formula (II) are those wherein the pyran ring is in the L-sorbopyranose absolute configuration, $R_6$ and $R_7$ are each hydrogen, $R_8$ and $R_9$ are each methyl; $R_{10}$ is methyl thiocarbonate ($CH_3SC(O)O$) and $R_{11}$ is halogen; or $R_{10}$ and $R_{11}$ are both halogen; or $R_{10}$ is hydroxyl and $R_{11}$ is halogen. Particularly preferred halogens include bromine, chlorine, and iodine.

Specific examples of compounds of formula (II) are: (1) 5-deoxy-5-iodo-2,3-O-(1-methylethylidene)-4-[methylthiocarbonyl)]-α-L-sorbopyranose sulfamate, (i.e., where the compound is in the L-sorbopyranose absolute configuration, $R_6$ and $R_7$ are hydrogen, $R_8$ and $R_9$ are methyl, $R_{10}$ is $CH_3SC(O)O$, and $R_{11}$ is iodine); (2) 4,5-dibromo-4,5-dideoxy-2,3-O-1-methylethylidene)-α-L-sorbopyranose sulfamate, (i.e., where the compound is in the L-sorbopyranose absolute configuration, $R_6$ and $R_7$ are hydrogen, $R_8$ and $R_9$ are methyl, $R_{10}$ and $R_{11}$ are bromine); and (3) 5-chloro-5-deoxy-2,3-O-(1-methylethylidene)-α-L-sorbopyranose sulfamate, (i.e., where the compound is in the L-sorbopyranose absolute configuration, $R_6$ and $R_7$ are hydrogen, $R_8$ and $R_9$ are methyl, $R_{10}$ is hydroxyl, and $R_{11}$ is chlorine).

Another compound useful in the practice of the invention is described in Formula III:

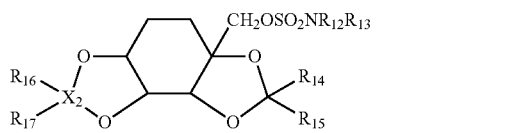
(Formula III)

wherein $R_{12}$ and $R_{13}$ are the same or different and are selected from any of hydrogen, alkyl ($C_1$ to $C_6$), cycloalkyl ($C_3$-$C_7$), allyl, or benzyl. In one embodiment, $R_{12}$ and $R_{13}$ are each hydrogen. $R_{14}$ and $R_{15}$ are the same or different and selected from hydrogen or lower alkyl.

$X_2$ may be chosen from carbon (C) or sulfur (S), with the stipulation that when $X_2$ is carbon, $R_{16}$ and $R_{17}$ are the same or different and are selected from hydrogen or lower alkyl, whereas when $X_2$ is sulfur one of $R_{16}$ and $R_{17}$ is oxygen and the other is a lone pair of electrons or both $R_{16}$ and $R_{17}$ are oxygen.

For compounds of formula III, the term alkyl includes straight and branched chains. For example, alkyl, radicals include methyl, ethyl, propyl, isopropyl, n-butyl, isbutyl, and t-butyl.

Particularly preferred compounds of formula III are: (I) (1R,2R,3S,4S)-(1,2:3,4-di-O-methylethylidenecyclohexan-1,2,3,4-tetraol-r-yl)methyl sulfamate, (i.e., where $R_{12}$ and $R_{13}$ are hydrogen, $R_{14}$, $R_{15}$, $R_{16}$, and $R_{17}$ are methyl and $X_2$ is carbon); (2) (1R,2R,3S,4S)-(3,4-O-methylenethylidene-1,2-O-sulfonyl-cyclohexan-1,2,3,4-tetraol-4-yl)methyl sulfamate, (i.e., where $R_{12}$ and $R_{13}$ are hydrogen, $R_{14}$ and $R_{15}$ are methyl, $R_{16}$ is oxygen and $R_{17}$ is an electron pair and $X_2$ is sulfur); and (3) (1R,2S,3S,4S)-(3,4-O-methylethylidene-1,2-O-sulfonyl-cyclohexan-1,2,3,4-tetraol-4-yl)methyl sulfamate, (i.e., where $R_{12}$ and $R_{13}$ are hydrogen, $R_{14}$ and $R_{15}$ are methyl, $R_{16}$ and $R_{17}$ are both oxygen and $X_2$ is sulfur).

Another compound useful in the subject invention is

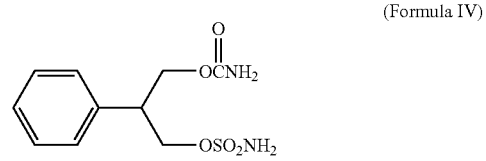
(Formula IV)

Other compounds useful in the practice of the invention include those of Formula V

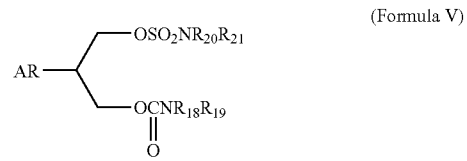
(Formula V)

wherein, AR is represented by the following formulas:

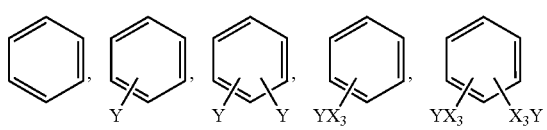

Y is selected from the group consisting of halogens such as F, Cl, Br and I, or trifluoromethyl and alkyl groups containing 1 to 3 carbon atoms when Y alone is attached to the benzene ring; when $X_3$, which may be S or O, is present, Y is selected from the group consisting of trifluoromethyl and alkyl groups containing 1 to 3 carbon atoms. $R_{18}$, $R_{19}$, $R_{20}$, and $R_{21}$, may be identical or different and are selected from the group consisting of hydrogen, linear or branched alkyl groups containing 1 to 16 carbon atoms, cyclic alkyl groups containing 3 to 16 carbon atoms and aryl groups containing 6 to 8 carbon atoms, and $NR_{18}R_{19}$ and $NR_{20}R_{21}$, identical or different, each may form a 3 to 7-membered aliphatic cyclic compound together with another nitrogen atom or oxygen atom.

Compositions useful in the practice of this invention comprise one or more of the compounds of formulas I-V admixed with a pharmaceutical carrier. The compositions may be made according to conventional pharmaceutical compounding techniques. Thus, the carrier may take a wide variety of forms depending on the form of preparation desired for administration, e.g., injection, oral, suppository, topical, or parenteral.

In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like.

Because of their ease in administration, tablets and capsules represent the most advantageous oral dosage unit form, in which case solid pharmaceutical carriers are employed. If desired, tablets may be sugar coated or enteric coated by standard techniques. Suppositories may be prepared, in which case cocoa butter could be used as the carrier.

For parenterals, the carrier will usually comprise sterile water, though other ingredients, for example, for purposes such as aiding solubility or for preservation, may be included. Injectable suspensions may also be prepared in which case appropriate liquid carriers, suspending agents and the like may be employed.

Other compositions useful in the practice of the subject invention include salves, cosmetics, ointments, and the like. Such compositions may be topically applied to a site or incorporated into articles of manufacture including, but not limited to, bandages, adhesive strips for the covering of wounds (e.g., BANDAID brand adhesive strips), or transdermal patches. Carriers such as cocoa butter, viscous polyethylene glycols, hydrogenated oils, and such mixtures can be emulsified if desired.

Compounds of the subject invention may also be incorporated into cosmetics. Additional materials and substances suitable as carriers for the compounds of formulas I-V are described in the International Cosmetic Ingredient Dictionary and Handbook, 8$^{th}$ Edition (The Cosmetic, Toiletry, and Fragrance Association (CTFA), 2000), hereby incorporated by reference in its entirety.

Where the pharmaceutical compositions are aerosols, the active ingredients can be packaged in pressurized aerosol containers with a propellant, e.g., carbon dioxide, nitrogen, propane, etc. with the usual adjuvants such as cosolvents, wetting agents, etc.

In accordance with the invention, pharmaceutical compositions comprise, as an inactive ingredient, an effective amount of one or more non-toxic, pharmaceutically acceptable ingredient(s). Examples of such ingredients for use in the compositions include ethanol, dimethyl sulfoxide, glycerol, silica, alumina, starch, calcium carbonate, talc, flour, and equivalent non-toxic carriers and diluents.

The pharmaceutical compositions herein will contain, per dosage unit, e.g., tablet, capsule, powder injection, teaspoonful, suppository, bandage, and the like, from about 0.1 to about 400 mg of the active ingredient. In a preferred embodiment, the compositions comprise about 100 mg to 200 mg per dosage unit. In an even more preferred embodiment, the compositions contain comprise about 20 mg to about 100 mg of active ingredient. In another embodiment, the compositions comprise about 25 mg of active ingredient per unit dose.

Topiramate is currently available for oral administration in round tablets containing 25 mg, 10 mg or 200 mg of active agent. The tablets contain the following inactive ingredients: lactose hydrous, pregelatinized starch, microcrystalline cellulose, sodium starch glycolate, magnesium stearate, purified water, carnauba wax, hydroxypropyl methyl cellulose, titanium dioxide, polyethylene glycol, synthetic iron oxide, and polysorbate 80.

It should be understood that the examples and embodiments described herein are for illustrative purposes only and that various modifications or changes in light thereof will be suggested to persons skilled in the art and are to be included within the spirit and purview of this application and the scope of the appended claims. All publications and patents cited herein are hereby incorporated by reference in their entireties.

EXAMPLE 1

Effects of Topiramate on Impulsivity and Cognitive Functioning

There are no reports of topiramate being utilized in PWS for any behavior. Measurements of attention, concentration, and impulsivity were assessed by the Delay and Vigilance tasks of the Gordon Diagnostic System (GDS; Gordon, M.; McClure, F. D.; & Aylward, G. P. (1996) *Gordon Diagnostic System, Interpretive Guide* (Third Edition); Dewitt, N.Y.: Gordon Systems, Inc.), a mechanized evaluator of cognitive functions, including attention and concentration. The GDS was originally developed, and most commonly used, to measure aspects of Attention-Deficit/Hyperactivity Disorder (ADHID) (previously called Attention-Deficit Disorder). One of the important components of the Vigilance test is the ability of an individual to have sustained attention, and the Delay task in part measures the subjects' ability to concentrate and focus on hitting a button at appropriate time intervals and delay impulsive behavioral responses.

The Delay Task requires that the subject inhibit responding (pressing a button and then refraining from pressing the button again for at least 6 seconds) in order to earn points. The Delay Task measures the subject's ability to suppress and delay impulsive behavioral responses. While focusing and sustaining attention usually facilitate Delay Task performance, the Delay Task maximally draws on a subject's ability to inhibit impulsive responses. The Delay Task's total efficiency ratio (EF) is considered the best indicator (score ranges from 0 to 1) of the level of impulsivity with the lower the score (such as less than 0.5) indicating higher impulsivity and poor self-control. The Vigilance Task measures the subject's ability to focus attention on a task and to maintain this attention over a period of time without reinforcement. The correct responses (CR) of the Vigilance Task measures the level of alertness and is a measure of the subjects attentional processes.

JAS-002 (patient Number 2) had a baseline total efficiency ratio (ER) of 0.02, approximately 8 standard deviations below the normal range and well below the first percentile in regards to the Delay task. This falls markedly within the range of an "abnormal" performance as stated in the rating score manual provided by the manufacturer of the GDS. At visit 4, approximately 1 month after starting medication (at a dose of 100 mg/day), JAS-002 demonstrated dramatic improvement in ER (a value of 0.98), well within the normal range of performance. At 2 months (at a dose of 175 mg/day), JAS-002 continued with improvements in ER (a value of 0.85), within the normal range of performance. Attention as evaluated by the Vigilance Task for JAS-002 showed essentially no change for CR from 39 at baseline to 38 (at a dose of 175 mg/day) at 2 months.

For patient Number 1 (MJG-001), a significant improvement has been noted. At baseline, MJG-001's ER for the Delay Task was at a value of 0.06 (approximately 7 standard deviations below the average ER) demonstrating a severe impairment of impulsivity. However, at the second testing session, MJG-001 showed moderate improvement with a Delay Task ER of 0.24. At visit 5, approximately 1.5 months after starting medication (at a dose of 75 mg/day), MJG-001 demonstrated a substantial improvement with an ER value of 0.46 and two weeks later (at a dose of 125 mg/day) had an ER value of 0.70. At 2 months after starting medication (at a dose of 150 mg/day), MJG-001 demonstrated a substantial improvement with an ER value of 0.50. The Vigilance Task for MJG-001 showed some variability up and down during the study and, after approximately 2 months, showed a mild decrease of CR from 43 to 41 (at a dose of 150 mg/day).

Patient Number 3 (GFV-003) has also shown a severe deficit in impulsivity and focusing; baseline ER was 0.02 (a value 8 standard deviations below the normal range). At visit 1, after one week at a low dose of topiramate (25 mg/day), GFV-003 had improved to an 0.09 ER and by week 4 (at a dose of 100 mg/day) to an ER of 0.19, and by 2 months (at a dose of 200 mg/day) the ER was at 0.10. The Vigilance Task for GFV-003 showed variability on topiramate and by the end of two months was essentially unchanged with a CR decreasing from 16 at baseline to 15 at 2 months.

Patient #4 (MCK-004) also showed abnormal performance on the Delay task (ER of 0.35). Within 1 week on low dose topiramate (25 mg/day) MCK-004 had improved to an ER of 0.51, by the $2^{nd}$ week on 50 mg/day topiramate, the ER was 0.76, and continued improvement by the $3^{rd}$ week on 75 mg/day with an ER of 0.65 and by two months at a dose of 150 mg/day, her ER continued to be improved at 0.64. The Vigilance Task for MCK-004 shows mild decrease from baseline CR of 38 to 34 (by the $8^{th}$ week on 150 mg/day).

Thus, the use of topiramate for impulsivity, without negative effects on attention and concentration, is both novel and clinically applicable. Disorders with impulsivity and deficits in attention and concentration are difficult to manage for both the patient and their caregiver, especially in cases of dementia. Impulsivity and lack of concentration can severely handicap day-to-day functioning in all age groups affected by these disorders. There are no reports in the literature of topiramate specifically used to treat impulsivity and/or deficits in attention and concentration.

EXAMPLE 2

Effect of Topiramate on Pathologic Skin Picking (PSP)

There are no reports of topiramate being utilized in PWS for any behavior. Patient #3 (GFV-003) also has pathologic skin picking (PSP) in addition to food seeking behavior. Patient #3 has a chronic large lesion on his lower left arm. Within one week of topiramate (25 mg/day), he had decreased skin picking and showed healing of this lesion on his left arm. By the $4^{th}$ week on topiramate (at 100 mg/day), the lesion on his lower left arm had completely healed over. The progression of wound healing is provided in FIGS. 9A-D and 12A-B.

Patient #1 (MJG-001) has pathologic skin picking (PSP) in addition to food seeking behavior. Unexpectedly and serendipitously, it was observed that several large lesions (where she skin picks) on her right arm, legs, and lips were clearing up quickly (within 5 days) after topiramate was initiated at 25 mg/day. Furthermore, the patient has continued to do well in terms of skin clearing. For example, a large lesion on her right arm completely healed over after about 2 months on topiramate (at a dose of 125 mg/day). The patient lives in a group home and workers there, as well as her mother, have also commented to us that her skin picking/skin has overall improved. The progression of wound healing is provided in FIGS. 10A-C and 11A-B.

The use of topiramate for PSP and related disorders is also novel and clinically applicable. There are no FDA approved pharmacological treatments for pathologic skin picking (also referred to as neurotic excoriation, repetitive skin picking, compulsive skin picking, and dermatotillomania) and possible related obsessive-compulsive spectrum disorders (i.e., repetitive self-mutilation (RSM), oncophagia, rhinotillxomania, trichotillomania) (Goldsmith, T. D.; Shapira, N. A.; Phillips, K. A.; et al., "Obsessive compulsive spectrum disorders"; in: Swinson, R. P.; Antony, M. M.; Rachman, S.; Richter, M. A. (Eds)., *Obsessive-Compulsive Disorder: Theory, Research, and Treatment*, Guilford Publications, New York, pp. 397-425 (1998)).

EXAMPLE 3

Effects of Topiramate on Patients with Prader-Willi Syndrome

In an 8-week, open-label, flexible-dose (maximum 350 mg/day) study to evaluate the efficacy and safety of topiramate in PWS adults, weekly evaluations were performed that included scales for stereotypical behavior (Stereotypy Checklist, Y-BOCS checklist), aberrant behavior (Aberrant Behavior Scale {ABS}, Severity of Symptoms Scale, Self-Injury and Self-Restraint Checklist) and cognitive functioning (Gordon Diagnostic, Controlled Oral Word Association Test, Semantic Naming test). Subject safety measures were also performed (e.g., monitoring blood pressure). Appetite was assessed for one hour at four time points during the trial. Measurements were made by investigator observation of the subject with free access to low calorie food and a visual analogue scale before and after observation.

Eight subjects (19-36 years of age; 4 males and 4 females) entered the trial and six have completed the treatment regimen. A mean weight loss of 0.3 pounds was observed over the course of the study. Appetite tests show a mean increase of 255.8 calories/hour; however, a dramatic reduction in self-injurious behavior was also observed (e.g., skin picking). Five subjects have continued long-term on topiramate for at least 6 months (mean of 8.2±1.5 months) and, in these subjects, there has been mean 4.9 lb±4.0 lb weight loss. Behavior evaluations have shown a reduction in aberrant behaviors (such as irritability and noncompliance [Mean ABS at baseline of 8.5±7.2 and mean ABS at week 8 of 5.3±5.1, *Z=−2.0, df=1, P=0.042 {Wilcoxon signed-ranks test}]) and self-injury in all four subjects exhibiting these behaviors. Healing of skin lesions was also observed. Open-label administration of topiramate has been shown to improve behavior and decrease self-injury in PWS subjects. Longer treatment lengths appear to result in steady weight decrease.

EXAMPLE 4

Effects of Topiramate on Prader-Willi Syndrome

In the above study was performed to assess the effects of topiramate on PWS. All subjects provided written informed consent for topiramate treatment and were between 18 and 65 years of age. Criteria for exclusion included: clinically significant suicidality or homicidality; current or recent (within 6 months of the start of topiramate) DSM-IV diagnosis of substance abuse or dependence; a clinically unstable disease that could interfere with treatment or assessment of PWS; treatment with any drug that might interact adversely with topiramate; and personal or family history of nephrolithiasis. Women of childbearing potential who were not taking adequate contraceptive measures were not included. Screening measures included a physical examination, psychiatric background, medication history, blood draw for laboratory assessment (CBC, SMA-12, urinalysis, and a B-hCG for women of childbearing potential), and the Structured Clinical Interview for DSM-IV, Patient Edition (SCID-P). Weekly assessments of weight loss, participant functioning, and safety measures including blood pressure and pulse were taken by the investigators at each visit. Participants are residents of group homes operated by the Association of Retarded Citizens, Alachua County, Florida (ARC). These homes are monitored, thereby allowing recording of participants' behavioral and psychiatric manifestations as well as their medication management. Participants began pharmacotherapy with topiramate at 25 mg of drug given in the evening for 7 days. After 14 days, their daily dose could be increased in increments of up to 50 mg/week for the next 6 weeks.

Case 1: Ms. A. is a 19 year-old female who through DNA methylation testing was positive for PWS and shown to have a chromosomal deletion through FISH and DNA polymorphism analyses. Ms. A. has a history of hoarding and severe skin picking dating to childhood. Current concomitant psychiatric medications include fluoxetine 60 mg/day and naltrexone 50 mg/day. Psychiatric intervention dated back to 1992 when the subject began therapy with clomipramine and fenfluramine, both of which were unsuccessful in managing her behavior and weight problem.

Initial side effects (of topiramate) experienced included mild sedation, word-finding difficulties, and unrelated lower back pain that resolved by Week 8. Ms. A's weight remained stable with a baseline of 129.5 lbs and weight of 128.5 lbs at Week 8. Ms. A had a long-standing primary lesion on her right forearm that measured approximately 4 cm by 1 cm and ulcerated at baseline. She experienced a reduction in skin picking with improvement to the lesions on her face, arm, and legs noted by Week 4 (75 mg/day). To better follow the improvement in her skin, a photographic record of Ms. A's lesion on her forearm was begun demonstrating healing of this lesion by Week 8 of topiramate (150 mg/day). See FIGS. 10A-C and 11A-B.

Case 2: Mr. B. is a 29 year-old male confirmed to be a chromosomal deletion as described above. He has a history of severe food seeking and skin picking dating to childhood. Mr. B does not have a history of taking psychotropic medications and had declined a previous recommendation to take fluoxetine. Initial healing of his primary lesion (a round 1.5 cm diameter ulcerated lesion) was noted within one week of initiating topiramate treatment (25 mg/day) at which point photographic records were started. Mr. B also experienced some increased irritability when topiramate was initiated. Irritability returned towards baseline by Week 8. Mr. B also experienced a decrease in his weight from 180.0 lbs at baseline to 176.8 lbs at Week 8. By Week 8 of topiramate (200 mg/day), Mr. B. had experienced remission of his self-injurious behavior (SIB) with resultant healing and complete unulceration of his primary lesion (FIGS. 9A-D and 12A-B).

Figure 13A:
FIGS. 13A-B: Photographs of primary SIB lesions. Ms. C. (right breast), baseline (FIG. 13A); Ms. C. on 175 mg/day (right breast), Week 8 (FIG. 13B).
Figure 13B:
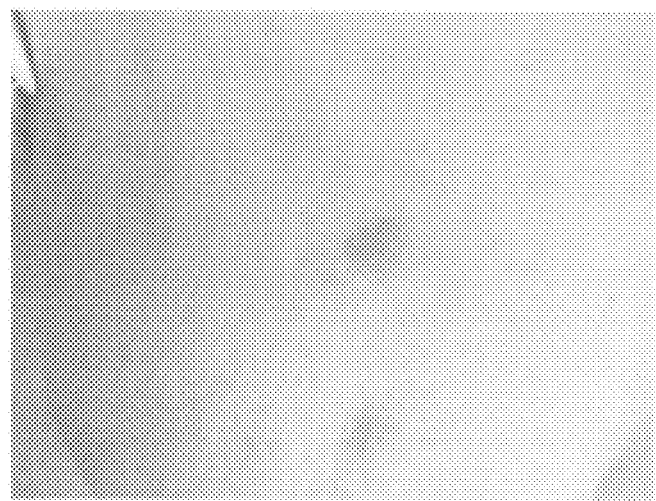

Case 3: Ms. C. is a 32 year-old female confirmed to be a chromosomal deletion. Concomitant psychotropic medications include fluoxetine 20 mg/day. She has a history of food seeking and skin picking dating to childhood. Due to her employment, Ms. C. picks in multiple concealed locations (e.g., her chest, breasts, and the top of her legs). Because of her secrecy regarding SIB, the staff members of her group home daily perform full body surveys. As a result of previous experience with Ms. A and Mr. B, photographic records of her lesions were started prior to initiation of topiramate (FIG. 13).

Figure 14:
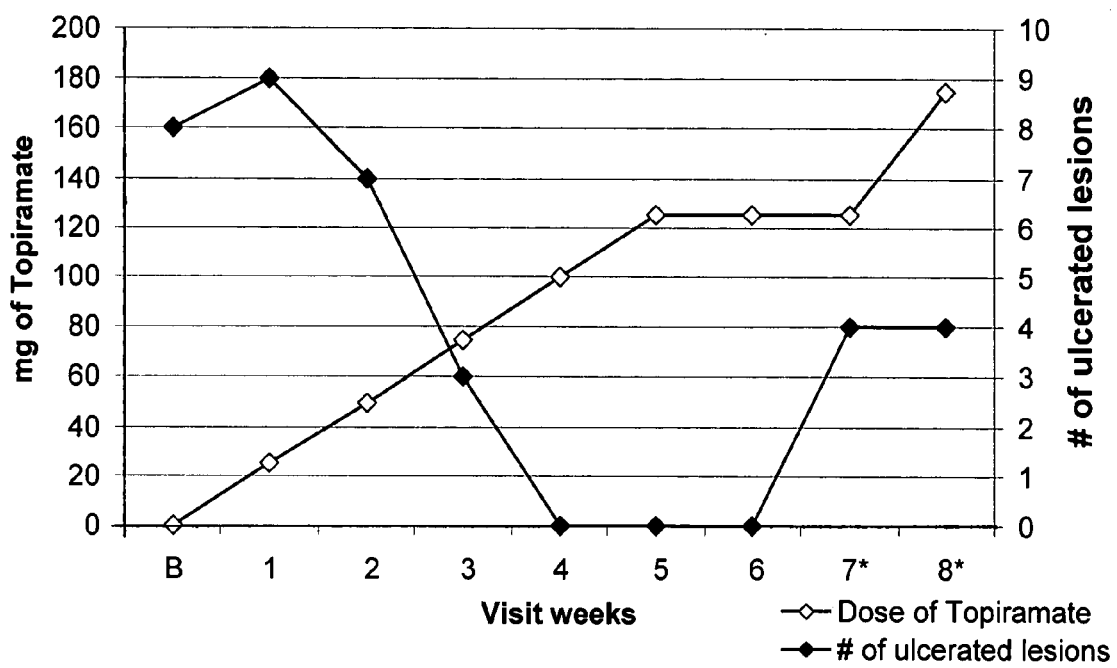
FIG. 14: Number of ulcerated SIB lesions for Ms. C. as documented by group home staff utilizing systematic full body surveys (* denotes lesions smaller than previous lesions and appearing to result after insect bites).
Figure 15A:
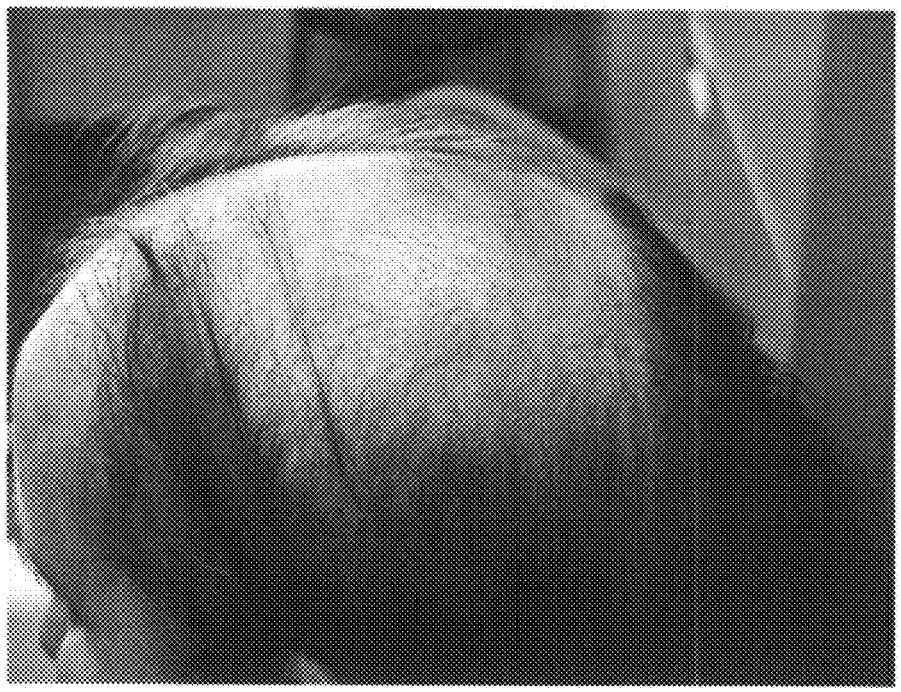
FIGS. 15A-B: Photographic record of Ms. A hair loss at start of treatment (FIG. 15A) and during treatment (FIG. 15B).
Figure 15B:

After beginning topiramate, an attenuation of SIB behavior and number of ulcerated lesions (FIG. 14) was noted within 1 week (25 mg/day) by photographs and by 2 weeks (50 mg/day) by her group home staff. Side effects included word-finding difficulty, mild confusion, sedation, and some mild tingling in her left heel. All side effects resolved by Week 5. On topiramate, Ms. C experienced an increased weight from 150 lbs at baseline to 154.5 lbs at Week 8. At Week 8, Ms. C. had continued attenuation of skin picking on a dose of 175 mg/day (FIGS. 14 and 15). During participation, Ms. C. experienced a period of three weeks where she was without any SIB. However, reportedly as result of her picking at several insect bites, small ulcerated lesions appeared on her forearm and lower legs in Weeks 7 and 8.

These three cases further illustrate the beneficial effects of the anti-epileptic drug topiramate. Topiramate is able to attenuate self-injurious behavior in a patient population where SIB is common and difficult to manage and treat. All three subjects have longstanding histories of self-injury, and two subjects (Ms. A. and C.) had failed previous psychotropic medication interventions. Furthermore, all three PWS subjects have chosen to continue on topiramate after the 8-week trial (8 months for Ms. A., 7 months for Mr. B., and 4 months for Ms. C.) with continued improvement in self-injury. Improvement in self-injury was noted by both investigators and in systematic body evaluations by the group home in one subject (Ms. C.). Additionally, while individuals with PWS often pick surreptitiously and pick even when they describe having no urges, all three subjects reported decreased urges to pick while on topiramate.

In terms of an objective measurement of impulsivity, subjects were also followed by the Delay Task of the computerized Gordon Diagnostic System (Gordon et al., 1996). The Delay Task measures a subject's ability to suppress and delay impulsive behavioral responses (Gordon et al., 1996). All three subjects demonstrated improvement in the Delay Task while on topiramate.

EXAMPLE 5

Effects of Topiramate on Impulsive Disorders in Mammals

Canine acral lick dermatitis (ALD), also known as lick granuloma, acral pruritic nodule, and neurodermatitis, is a common self-inflicted skin disorder in dogs in which localized alopecia and epidermal hyperplasia and fibrosis are caused by continued licking, biting, and/or scratching one or more areas usually near the carpus or hock. When severe, the licking of the paws or flank causes significant local trauma and, in extreme cases, may require surgery and steroids. Occasionally, the animal must be put to death because of chronic ulceration or osteomyelitis. The etiology of ALD is unknown, although, commonly, it is considered to be psychogenic in origin secondary to boredom, loneliness, or confinement. It can also be provoked by local irritation. Certain large breeds appear to be more susceptible, such as German Shepherds, Labrador Retrievers, and Great Danes. The repetitive self-licking, chewing, or scratching creates areas of hair loss and the production of lesions which may range in size from several centimeters to the entire surface of the limb. This stereotypic behavior prevents the lesions from healing and may cause discomfort, pain and, in severe cases, may prove crippling.

Twenty dogs will be recruited from the Veterinary Animal Teaching Hospital. Other causes of licking will be ruled out by examining the dogs' clinical history, typical lesion appearance, and past history of treatment response. Dogs must exhibit chronic licking of 6 months or more that has caused an observable lesion(s). Reasons for exclusion from the study include: dogs undergoing concurrent treatment for ALD, dogs weighing <5 kg, dogs that have not been neutered or spayed, nephrolithiasis, and a significant acute or chronic confounding disease. Once the referring veterinarian has consented to the dogs' involvement, letters inviting participation in the study will be sent out to the owners of appropriate candidates. An informed consent documents will also be obtained.

A double-blind placebo-controlled trial of 8 weeks duration (6 week treatment and 2 week taper) will be conducted. One-half of the dogs receive placebo. The dogs will start at 2 mg/kg in a split dose (1 mg/kg twice a day) for the first two weeks. The dose will be increased 2 mg/kg a week as tolerated for the next four weeks. Thus, the maximum dosage will not exceed 10 mg/kg. This dosage strategy is based upon the target dose for seizures, which is 5 to 10 mg/kg in split doses.

Topiramate or placebo will be administered via gelatin capsules once daily (5 minutes before feeding). Owners will be instructed to avoid feeding dogs anything in addition to their regular diet. In addition to adhering to the dogs' routine (e.g., food, exercise, and training), owners will also be asked to maintain environmental conditions for the duration of the study.

A video camera will record the dogs' behavior for 1 hour each week for the 6 weeks of the trial. The primary behavior of interest is self-licking or self-chewing of the granulomatous lesion. The measure of time the dogs are involved in licking or chewing will be computerized. The evaluator will press the designated key when the dog's tongue or lips first makes contact with the lesion, and at the end of a continuous bout of licking or chewing when the dog lifts its head from the lesion and transfers its attention elsewhere.

In addition to videotaping, the owners will rate their dogs' licking behavior on a 10-point scale, with 10 being the worst ever observed and 0 indicating a complete absence of excess licking (Acral Lick Dermatitis Severity Scale). Investigators will also rate the dogs' behavior using a similar scale. Finally, photographs of the lesions will be taken weekly. Additionally, at baseline, a checklist for phobias will be done with the owners and the list will be reviewed each week using clinical global impression scales to rate phobias.

A 2-week taper period will follow the 6-week treatment period. During week 7, study medication will be reduced by approximately 25% for 3 days. On day 4, the dosage will be reduced by another 25%. On day 11 the remaining dose will be reduced in half again and on day 13 all study medication will be stopped. The dogs' last visit will be day 14 of the taper period.

For each of the efficacy measures, a listing of each patient's score at each study week during treatment will be generated. The evaluation of change in efficacy measurements will be carried out using standard analysis of variance techniques. All statistical tests will be two-sided if not otherwise specified. A test will be said to be significant if p<0.05. Analyses will be preformed using the "intent-to-treat" population consisting of all dogs randomized into the trial that take at least one capsule of study medication and had at least one post-baseline evaluation. The primary efficacy variable will be the number of self-injurious behaviors observed by video camera during weekly visits. A dog's self injury duration (in min/hr) is measured at the baseline and six weeks after treatment. The improvement score is the percentage of reduction (in ratio), i.e., improvement=(baseline−posttreatment)/baseline.

EXAMPLE 6

Effects of Topiramate on Trichotillomania

Topiramate was used as an adjunct therapy in a 38 year-old female with a 9-year history of trichotillomania. She was on a stable dose combination of fluvoxamine and clomipramine. While the fluvoxamine/clomipramine combination was therapeutic for 3 years, 6 months ago Ms. A experienced an increase in hair pulling predominately on the left side of her head. The investigators have made photographic records of Ms. A's hair loss (FIGS. 15A-B) and she has been evaluated psychometrically for impulse control. Ms. A was started on a 25 mg dose of topiramate at night and was gradually titrated in increments of 25 mg to 150 mg at night. Preliminary results suggest the addition of topiramate to this combination therapy effective for trichotillomania.

Figure 16:
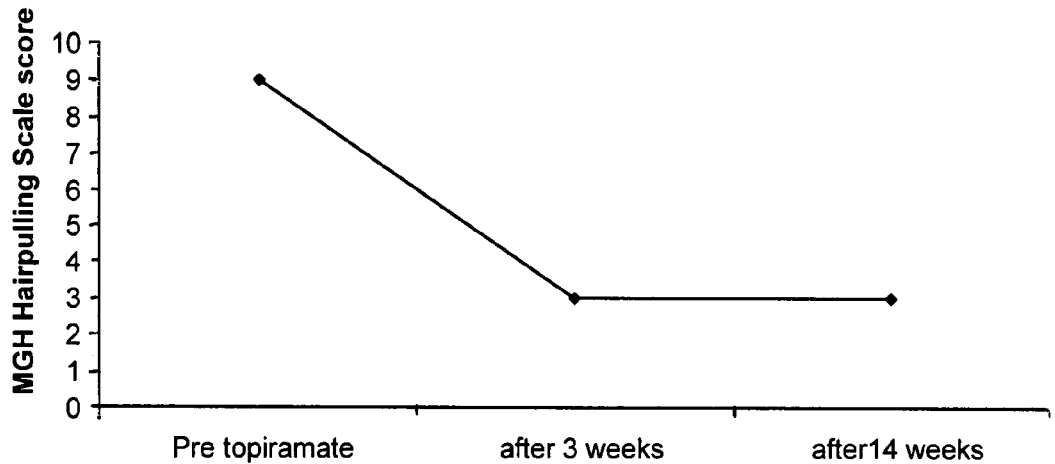
FIG. 16 illustrates the reported reduction in the urge of Ms. A to pull hair.

Before topiramate was initiated, clomipramine blood levels were as follows: clomipramine=354 ng/ml, DM clomipramine=118 ng/ml, and clomipramine+DM clomipramine=472 ng/ml. Following the addition of topiramate Ms. A reported a lessening of the urges to pull her hair starting at a relatively low dose (approximately 50 mg/day). Ms. A reported a significant reduction in the urge to pull by 3 weeks following the addition of topiramate and this improvement has been maintained for 14 weeks (FIG. 16). Although patient described decreased urges to pull hair, her re-growth was minimal. Subsequent laboratory assessments when patient was on 150 mg of topiramate, 100 mg of clomipramine and 50 mg of fluvoxamine showed that although the ratio of parent to metabolite were the same as before topiramate (0.69), both measurements were elevated: clomipramine=514 ng/ml, DM clomipramine 181 ng/ml, clomipramine+DM clomipramine=695 ng/ml.

After initial success with topiramate augmentation, the patient is currently being weaned off clomipramine and is currently on 25 mg/day from 100 mg/day without any increase in urges to hair pull. Ms. A has experienced weight loss of approximately 5 lbs which she reports as a positive side effect. Possible other side effects of topiramate administration include disruption of attention and concentration and cognitive deficits such as word finding difficulties.

Figure 17:
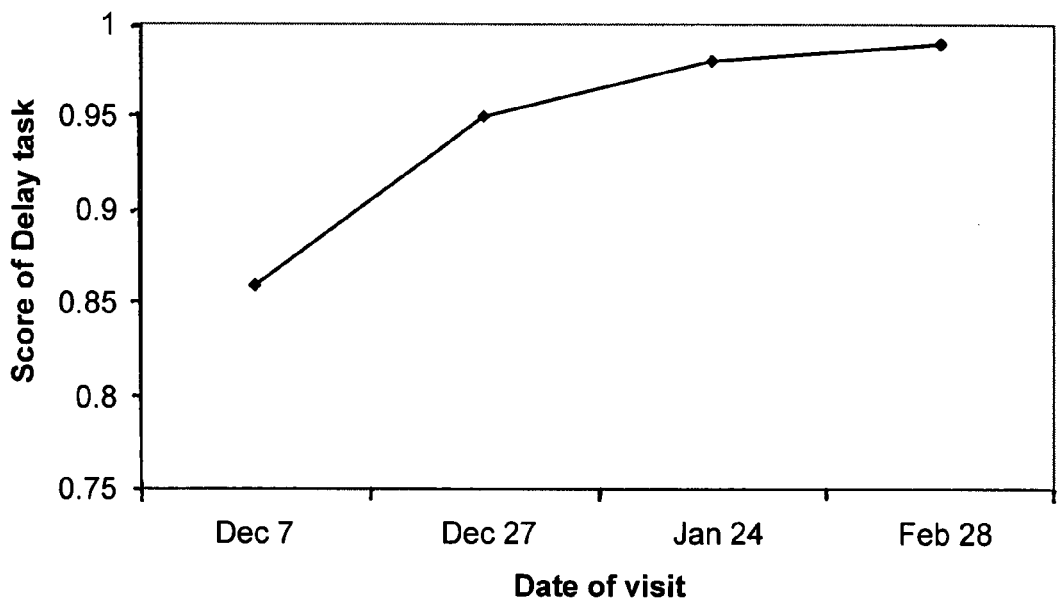
FIG. 17 represents the improvement in impulse control for Ms. A during treatment using the Gordon Diagnostic System.
Figure 18:
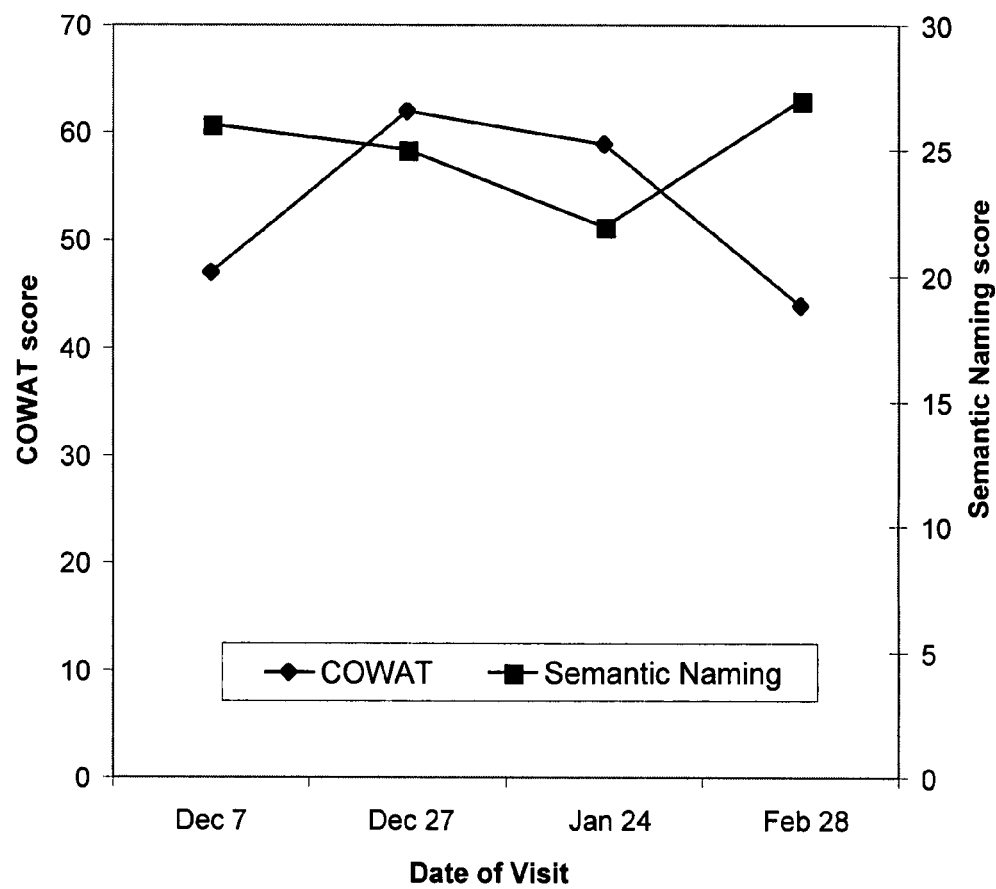
FIG. 18 illustrates that Ms. A suffered no significant change in cognitive ability during treatment.

Ms. A has been evaluated psychometrically for these side effects. Results from the Delay task of the Gordon Diagnostic System, a widely used measurement of impulse control, have shown improvements from baseline (FIG. 17). Subsequent testing of word finding abilities through the Control Oral Word Association Test (COWAT) and Semantic Category Naming test have shown no significant changes from baseline (FIG. 18).

The patient has continued to see a reduction in the urge to, as well as in the time spent, pull her hair. Re-growth of hair at the sites previously pulled has also been observed. The patient is currently on 475 mg topiramate (p.o. q.h.s.).

EXAMPLE 7

Effects of Topiramate on Trichotillomania

A 19-year-old female with a history of trichotillomania and skin picking has also been treated in accordance with the invention. She presented with skin lesions on her hands and face that resulted from picking at pimples (face) and pulling of hair on the backs of her hands. Several medications, in various classes, were previously tried without improvement (including mirtazapine, citalopram, gabapentin, paroxetine, nefazadone, and sertaline). The initiation of topiramate has resulted in the resolution of her trichotillomania, with noticeable re-growth of hair on the backs of her hands at 200 mg. p.o. q.h.s.) and has also resulted in improvements in the facial skin lesions. She is currently on 300 mg q.d. topiramate monotherapy.

We claim:

1. A method of promoting wound healing comprising:
   a) providing an individual having a skin wound; and
   b) topically administering, to said individual, a therapeutically effective amount of a composition comprising topiramate thereby promoting healing of said skin wound.

2. The method according to claim 1, wherein said composition is topically administered to a wound site as a component of a salve, an ointment, an aerosol, a bandage, a transdermal patch, a wound dressing, a cosmetic, or a bioadhesive.

3. The method according to claim 1, wherein the dosage of topiramate is: a) 0.1 mg to about 400 mg; b) about 10 mg to about 200 mg; c) about 20 mg to about 100 mg; or d) about 25 mg.

* * * * *